United States Patent [19]
Rufener, II et al.

[11] Patent Number: 5,563,316
[45] Date of Patent: Oct. 8, 1996

[54] MAIZE CHLOROTIC DWARF VIRUS RESISTANT MAIZE AND THE PRODUCTION THEREOF

[75] Inventors: George K. Rufener, II, Johnston; Albert J. Balducchi; Ronald P. Mowers, both of Ames, all of Iowa; Richard C. Pratt; Raymond Louie, both of Wooster, Ohio; Michael McMullen, Columbia, Mo.; John Knoke, Wooster, Ohio

[73] Assignee: Zeneca Limited, London, England

[21] Appl. No.: 298,592

[22] Filed: Aug. 31, 1994

Related U.S. Application Data

[63] Continuation-in-part of Ser. No. 235,028, Apr. 28, 1994, abandoned.

[51] Int. Cl.[6] .................................. A01H 5/00; A01H 1/00
[52] U.S. Cl. .................. 800/200; 800/250; 800/DIG. 56; 435/172.3; 435/172.1; 47/58; 47/DIG. 1
[58] Field of Search ..................................... 800/200, 205, 800/250, DIG. 56; 47/58.03, 58.05; 435/172.3

[56] References Cited

U.S. PATENT DOCUMENTS 5,220,114  6/1993  Martin ..................................... 800/200

OTHER PUBLICATIONS

Fisher et al. (1992) 1992 Ohio and West Virginia performance tests to virus–tolerant corn hybrids exposed to natural MDMV and MCDV infections. The Ohio State University Extension.

Guthrie et al. (1982) European corn borer and maize chlorotic dwarf virus resistance susceptibility in inbred lines of dent maize, pp. 221–233, *Maydica*, vol. XXVII.

Hunt et al. (1988) Evidence for infectivity of maize chlorotic dwarf virus and for a helper component in its leaf hopper transmission, pp. 499–504. Phytopathology, vol. 78, No. 4.

Lipps et al. (1992) Corn virus control and herbicide usage, *Plant Pathology Notes*.

Pratt et al. (1992) Symptom expression of maize inbred and hybrids infected by severe and type strain of maize chlorotic dwarf virus, Poster presented at the 84th Annual Meeting of the Crop Science Society of America, Nov. 5, 1992.

Williams et al. (1984) Registration of Mp705, Mp706, and Mp707 germplasm lines of maize, p. 1217. *Crop Science*, vol. 24 (6), Nov.–Dec.

Louie et al. (1990) *Elite Maize Germplasm: reaction to Maize Dwarf Mosaic and Maize Chlorotic Dwarf Viruses*, Crop Science. vol. 30, pp. 1210–1215.

McMullen et al. (1991) *Identification of a gene for resistance to Wheat Streak Moasic Virus in Maize*. Phytopathology vol. 81, pp. 624–627.

*Primary Examiner*—Gary Benzion
*Attorney, Agent, or Firm*—Dana Rewoldt

[57] ABSTRACT

The present invention provides a maize plant, method of making and using the same, which is resistant to Maize Chlorotic Dwarf Virus (MCDV). More particularly the invention relates to the introgression into elite maize lines genetic material identified by map loci which is capable of causing the plant and hybrid produced therefrom to be resistant to MCDV.

4 Claims, 26 Drawing Sheets

FIG. 1

```
                          MCDV  DATA
REGRESSION BY ADJACENT PAIR - ADDITION OF ADJACENT PAIRS REG. COEFF
              Y = VA35          Z = MP705
          ESTIMATES CORRESPOND TO  (YY-ZZ)/2
              DIST = RECOMBINATION I
```

| CHROM | PROBE1 | PROBE2 | DIST | VEINB SUM | VEINB STD | VEINB DIST PROPOR | TWIST T SUM | TWIST T STD | TWIST T DIST PROPOR | CHLOR SUM | CHLOR STD | CHLOR DIST PROPOR |
|---|---|---|---|---|---|---|---|---|---|---|---|---|
| 1 | N0406 E | U0076 A | 22.8 | 0.06 | 0.15 | 0.32 | 0.07 | 0.09 | 0.71 | 0.10 | 0.12 | 0.93 |
| 1 | U0076 A | N0234 B | 33.7 | -0.16 | 0.14 | 0.72 | 0.02 | 0.08 | 0.43 | -0.03 | 0.12 | 0.54 |
| 1 | N0234 B | U0013 E | 27.6 | -0.08 | 0.14 | 0.43 | 0.07 | 0.08 | 0.65 | 0.01 | 0.11 | 0.52 |
| 1 | U0013 E | B1206 D | 11.9 | 0.17 | 0.13 | 0.72 | 0.16 | 0.07 | 0.68 | 0.14 | 0.10 | 0.12 |
| 1 | B1206 D | N0401 A | 29.3 | 0.26 | 0.15 | 0.53 | 0.18 | 0.08 | 0.22 | 0.19 | 0.12 | 0.65 |
| 1 | N0401 A | U0167 E | 27.2 | 0.34 | 0.15 | 0.67 | 0.22 | 0.09 | 0.89 | 0.28 | 0.12 | 0.66 |
| 1 | U0167 E | U0067 C | 28.8 | 0.37 | 0.13 | 0.90 | 0.27 | 0.08 | 0.78 | 0.32 | 0.11 | 0.98 |
| 1 | U0067 C | U0119 B | 15.2 | 0.40 | 0.14 | 0.25 | 0.30 | 0.08 | 0.34 | 0.35 | 0.11 | 0.21 |
| 1 | U0119 B | U0033 B | 26.4 | 0.15 | 0.15 | 0.34 | 0.16 | 0.09 | 0.24 | 0.13 | 0.12 | 0.35 |
| 1 | U0033 B | N0447 B | 19.8 | 0.11 | 0.15 | 0.65 | 0.10 | 0.09 | 0.79 | 0.13 | 0.12 | 0.66 |
| 1 | N0447 B | N0120 D | 12.6 | 0.27 | 0.13 | 0.40 | 0.12 | 0.08 | 0.09 | 0.23 | 0.10 | 0.01 |
| 1 | N0120 D | U0107 B | 26.9 | 0.41 | 0.16 | 0.59 | 0.19 | 0.09 | 0.74 | 0.36 | 0.12 | 0.72 |
| 1 | U0107 B | B0725 D | 20.5 | 0.21 | 0.14 | 0.27 | 0.13 | 0.08 | 0.18 | 0.24 | 0.11 | 0.20 |
| 1 | B0725 D | U0084 B | 12.8 | 0.17 | 0.14 | 0.72 | 0.13 | 0.08 | 0.83 | 0.19 | 0.11 | 0.81 |
| 1 | U0084 B | N0238 B | 10.7 | 0.16 | 0.14 | 0.31 | 0.10 | 0.08 | 0.31 | 0.18 | 0.11 | 0.24 |
| 3 | B0815 B | N0446 D | 38.7 | 0.26 | 0.15 | 0.54 | 0.15 | 0.09 | 0.84 | 0.15 | 0.12 | 1.00 |
| 3 | N0446 D | U0050 A | 5.1 | 0.35 | 0.14 | 0.87 | 0.25 | 0.08 | 0.77 | 0.35 | 0.11 | 0.91 |
| 3 | U0050 A | N0296 D | 16.5 | 0.28 | 0.16 | 0.13 | 0.25 | 0.09 | 0.15 | 0.34 | 0.12 | 0.03 |
| 3 | N0296 D | U0060 E | 16.6 | 0.06 | 0.17 | 0.63 | 0.10 | 0.10 | 0.12 | 0.09 | 0.14 | 0.02 |
| 3 | U0060 E | B1520 D | 25.7 | 0.12 | 0.17 | 0.73 | 0.06 | 0.10 | 0.73 | 0.12 | 0.14 | 0.96 |
| 3 | B1520 D | U0063 C | 42.6 | 0.06 | 0.16 | 0.27 | 0.01 | 0.09 | 0.48 | 0.11 | 0.13 | 0.09 |
| 3 | U0063 C | U0096 D | 15.4 | -0.09 | 0.14 | 0.65 | -0.08 | 0.08 | 0.85 | -0.02 | 0.11 | 0.55 |
| 3 | U0096 D | N0457 B | 5.9 | -0.08 | 0.13 | 0.37 | -0.04 | 0.08 | 0.38 | -0.00 | 0.11 | 0.50 |
| 3 | N0457 B | U0026 D | 55.0 | -0.32 | 0.15 | 0.87 | -0.21 | 0.08 | 0.87 | -0.19 | 0.12 | 0.77 |
| 4 | U0031 A | N0386 A | 21.5 | -0.05 | 0.15 | 0.59 | -0.03 | 0.09 | 0.56 | 0.01 | 0.12 | 0.47 |
| 4 | N0386 A | U0042 E | 11.6 | -0.26 | 0.15 | 0.68 | -0.18 | 0.09 | 0.46 | -0.17 | 0.12 | 0.79 |
| 4 | U0042 E | N0396 B | 7.8 | -0.30 | 0.14 | 0.54 | -0.18 | 0.08 | 0.68 | -0.23 | 0.11 | 0.65 |
| 4 | N0396 B | U0066 A | 17.0 | -0.28 | 0.14 | 0.34 | -0.18 | 0.08 | .032 | -0.20 | 0.12 | 0.09 |
| 4 | U0066 A | U0019 D | 7.7 | -0.24 | 0.13 | 0.64 | -0.16 | 0.08 | 0.71 | -0.14 | 0.11 | 0.80 |
| 4 | U0019 D | U0127 E | 14.6 | -0.32 | 0.16 | 0.51 | -0.20 | 0.09 | 0.39 | -0.24 | 0.13 | 0.62 |
| 4 | U0127 E | N0444 B | 14.0 | -0.24 | 0.16 | 0.22 | -0.15 | 0.09 | 0.39 | -0.22 | 0.13 | 0.32 |
| 4 | N0444 B | U0052 B | 17.0 | 0.08 | 0.16 | 0.61 | 0.04 | 0.09 | 0.57 | 0.09 | 0.13 | 0.60 |
| 4 | U0052 B | N0451 B | 36.1 | 0.27 | 0.17 | 0.37 | 0.11 | 0.10 | 0.03 | 0.26 | 0.13 | 0.30 |
| 5 | N0213 B | N0409 D | 54.5 | 0.17 | 0.18 | 0.86 | 0.03 | 0.10 | 0.63 | 0.11 | 0.14 | 0.74 |
| 5 | N0409 D | U0072AE | 16.3 | 0.23 | 0.15 | 0.15 | 0.01 | 0.09 | 0.46 | 0.15 | 0.12 | 0.13 |
| 5 | U0072AE | B0502 E | 45.1 | 0.05 | 0.17 | 0.31 | -0.08 | 0.10 | 0.53 | 0.05 | 0.14 | 0.61 |
| 5 | B0502 E | N0295 A | 17.3 | 0.02 | 0.15 | 0.56 | 0.00 | 0.09 | 0.50 | 0.08 | 0.12 | 0.93 |
| 5 | N0295 A | B0571 B | 12.2 | 0.13 | 0.15 | 0.88 | 0.09 | 0.08 | 0.46 | 0.14 | 0.12 | 0.76 |
| 5 | B0571 B | U0054 C | 19.8 | 0.31 | 0.14 | 0.74 | 0.15 | 0.08 | 0.74 | 0.30 | 0.11 | 0.74 |
| 5 | U0054 C | U0126 A | 8.1 | 0.41 | 0.13 | 0.49 | 0.23 | 0.07 | 0.92 | 0.41 | 0.10 | 0.44 |
| 5 | U0126 A | N0239 A | 10.5 | 0.42 | 0.14 | 0.17 | 0.30 | 0.08 | 0.39 | 0.38 | 0.11 | 0.05 |
| 5 | N0239 A | U0108 E | 25.9 | 0.14 | 0.17 | 0.25 | 0.18 | 0.10 | 0.02 | 0.18 | 0.13 | 0.21 |
| 5 | U0108 E | N0288 A | 24.2 | 0.18 | 0.17 | 0.80 | 0.18 | 0.10 | 0.88 | 0.19 | 0.13 | 0.74 |
| 5 | N0288 A | U0104 B | 18.8 | 0.17 | 0.15 | 0.25 | 0.14 | 0.09 | 0.15 | 0.12 | 0.12 | 0.19 |
| 7 | N0391 D | B1540 D | 18.2 | 0.33 | 0.20 | 0.16 | 0.15 | 0.12 | 0.23 | 0.32 | 0.16 | 0.07 |
| 7 | B1540 D | U0016 E | 19.5 | -0.06 | 0.15 | 1.00 | -0.03 | 0.09 | 0.18 | 0.03 | 0.12 | 0.56 |
| 7 | U0016 E | B1521 B | 15.6 | 0.04 | 0.15 | 0.55 | 0.06 | 0.09 | 0.62 | 0.11 | 0.12 | 0.69 |
| 7 | B1521 B | N0455 D | 10.9 | 0.28 | 0.15 | 0.62 | 0.17 | 0.09 | 0.42 | 0.24 | 0.12 | 0.51 |
| 7 | N0455 D | U0056 A | 9.3 | 0.29 | 0.15 | 0.41 | 0.21 | 0.09 | 0.70 | 0.24 | 0.12 | 0.46 |
| 7 | U0056 A | U0110 C | 10.5 | 0.20 | 0.12 | 0.83 | 0.18 | 0.07 | 0.55 | 0.18 | 0.10 | 0.87 |
| 7 | U0110 C | B1407 E | 14.4 | 0.13 | 0.13 | 0.36 | 0.13 | 0.07 | 0.28 | 0.15 | 0.10 | 0.19 |
| 7 | B1407 E | N0433 B | 21.5 | 0.12 | 0.14 | 0.85 | 0.09 | 0.08 | 0.58 | 0.17 | 0.11 | 0.84 |
| 10 | B0304 A | N0264 A | 55.0 | 0.22 | 0.15 | 0.67 | 0.12 | 0.09 | 0.67 | 0.28 | 0.12 | 0.77 |
| 10 | N0264 A | U0064 B | 23.5 | 0.59 | 0.15 | 0.42 | 0.37 | 0.09 | 0.55 | 0.54 | 0.12 | 0.39 |
| 10 | U0064 B | N0445 B | 13.8 | 0.52 | 0.15 | 0.47 | 0.32 | 0.08 | 0.28 | 0.46 | 0.12 | 0.48 |
| 10 | N0445 B | N0285 E | 27.8 | 0.22 | 0.14 | 0.30 | 0.12 | 0.08 | 0.26 | 0.21 | 0.11 | 0.26 |
| 10 | N0285 E | U0044 A | 50.0 | 0.14 | 0.19 | 0.95 | 0.16 | 0.11 | 0.91 | 0.16 | 0.15 | 0.78 |

FIG. 2A

MCDV DATA

Y = SUSCEPTIBLE

* = SIGNIFICANT AT .05 LEVEL    ** = SIGNIFICANT AT .01 LEVEL OR LOWER

REALLY COMBINED DATA –                     – NO ESCAPES INCLUDED

| U0167_E GENOTYPE | VEINB MEAN | STD ERR | TWIST_T* MEAN | STD ERR | CHLOR MEAN | STD ERR | CUM MEAN | STD ERR | N |
|---|---|---|---|---|---|---|---|---|---|
| YY | 3.35 | 0.16 | 2.16 | 0.11 | 2.87 | 0.15 | 8.39 | 0.40 | 47 |
| YZ | 3.06 | 0.12 | 1.88 | 0.08 | 2.58 | 0.11 | 7.52 | 0.30 | 82 |
| ZZ | 2.87 | 0.21 | 1.68 | 0.14 | 2.43 | 0.19 | 6.98 | 0.51 | 29 |

| B0559_B GENOTYPE | VEINB* MEAN | STD ERR | TWIST_T* MEAN | STD ERR | CHLOR* MEAN | STD ERR | CUM MEAN | STD ERR | N |
|---|---|---|---|---|---|---|---|---|---|
| YY | 3.38 | 0.21 | 2.22 | 0.15 | 2.85 | 0.20 | 8.45 | 0.53 | 23 |
| YZ | 3.11 | 0.16 | 1.87 | 0.11 | 2.66 | 0.16 | 7.64 | 0.41 | 39 |
| ZZ | 2.58 | 0.24 | 1.56 | 0.16 | 2.05 | 0.22 | 6.19 | 0.58 | 39 |

| U0067_C GENOTYPE | VEINB** MEAN | STD ERR | TWIST_T** MEAN | STD ERR | CHLOR** MEAN | STD ERR | CUM** MEAN | STD ERR | N |
|---|---|---|---|---|---|---|---|---|---|
| YY | 3.54 | 0.20 | 2.30 | 0.14 | 3.06 | 0.18 | 8.90 | 0.49 | 30 |
| YZ | 3.16 | 0.11 | 1.94 | 0.08 | 2.66 | 0.10 | 7.76 | 0.27 | 96 |
| ZZ | 2.67 | 0.18 | 1.62 | 0.12 | 2.21 | 0.16 | 6.50 | 0.43 | 39 |

| U0119_B GENOTYPE | VEINB* MEAN | STD ERR | TWIST_T** MEAN | STD ERR | CHLOR** MEAN | STD ERR | CUM** MEAN | STD ERR | N |
|---|---|---|---|---|---|---|---|---|---|
| YY | 3.43 | 0.18 | 2.27 | 0.12 | 2.97 | 0.16 | 8.67 | 0.45 | 40 |
| YZ | 3.01 | 0.15 | 1.84 | 0.10 | 2.47 | 0.13 | 6.49 | 0.36 | 61 |
| ZZ | 2.63 | 0.23 | 1.65 | 0.15 | 2.21 | 0.20 | 6.49 | 0.55 | 26 |

| U0033_B GENOTYPE | VEINB* MEAN | STD ERR | TWIST_T MEAN | STD ERR | CHLOR MEAN | STD ERR | CUM* MEAN | STD ERR | N |
|---|---|---|---|---|---|---|---|---|---|
| YY | 3.45 | 0.18 | 2.12 | 0.13 | 2.86 | 0.17 | 8.43 | 0.45 | 33 |
| YZ | 2.92 | 0.15 | 1.82 | 0.11 | 2.52 | 0.14 | 7.27 | 0.38 | 47 |
| ZZ | 3.52 | 0.18 | 2.10 | 0.13 | 2.97 | 0.17 | 8.60 | 0.44 | 35 |

| N0447_B GENOTYPE | VEINB** MEAN | STD ERR | TWIST_T MEAN | STD ERR | CHLOR** MEAN | STD ERR | CUM** MEAN | STD ERR | N |
|---|---|---|---|---|---|---|---|---|---|
| YY | 3.41 | 0.15 | 2.07 | 0.10 | 2.88 | 0.14 | 8.36 | 0.36 | 54 |
| YZ | 3.12 | 0.12 | 1.90 | 0.08 | 2.54 | 0.11 | 7.56 | 0.29 | 86 |
| ZZ | 2.62 | 0.18 | 1.68 | 0.13 | 2.21 | 0.17 | 6.50 | 0.45 | 35 |

| N0120_D GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.49 | 0.17 | 2.02 | 0.12 | 2.83 | 0.16 | 8.34 | 0.43 | 38 |
| YZ | 3.06 | 0.12 | 1.88 | 0.08 | 2.54 | 0.11 | 7.48 | 0.30 | 79 |
| ZZ | 2.96 | 0.21 | 1.82 | 0.14 | 2.47 | 0.19 | 7.26 | 0.52 | 26 |

| U0107_B GENOTYPE | VEINB* MEAN | STD ERR | TWIST_T* MEAN | STD ERR | CHLOR** MEAN | STD ERR | CUM** MEAN | STD ERR | N |
|---|---|---|---|---|---|---|---|---|---|
| YY | 3.40 | 0.15 | 2.09 | 0.10 | 2.93 | 0.13 | 8.43 | 0.36 | 56 |
| YZ | 3.08 | 0.13 | 1.98 | 0.09 | 2.58 | 0.12 | 7.64 | 0.32 | 73 |
| ZZ | 2.61 | 0.22 | 1.56 | 0.15 | 2.17 | 0.20 | 6.35 | 0.54 | 25 |

| B0725_D GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.44 | 0.17 | 2.09 | 0.12 | 2.91 | 0.16 | 8.45 | 0.42 | 39 |
| YZ | 3.17 | 0.13 | 1.95 | 0.09 | 2.58 | 0.11 | 7.70 | 0.31 | 72 |
| ZZ | 2.99 | 0.19 | 1.81 | 0.13 | 2.47 | 0.17 | 7.27 | 0.46 | 33 |

| U0084_B GENOTYPE | VEINB** MEAN | STD ERR | TWIST_T** MEAN | STD ERR | CHLOR** MEAN | STD ERR | CUM** MEAN | STD ERR | N |
|---|---|---|---|---|---|---|---|---|---|
| YY | 3.22 | 0.15 | 2.00 | 0.10 | 2.75 | 0.14 | 7.97 | 0.36 | 53 |
| YZ | 3.41 | 0.13 | 2.12 | 0.09 | 2.88 | 0.12 | 8.41 | 0.32 | 66 |
| ZZ | 2.60 | 0.18 | 1.56 | 0.13 | 2.14 | 0.17 | 6.29 | 0.45 | 34 |

| N0238_B GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.32 | 0.16 | 1.99 | 0.11 | 2.78 | 0.15 | 8.09 | 0.39 | 48 |
| YZ | 3.16 | 0.13 | 1.93 | 0.09 | 2.58 | 0.12 | 7.67 | 0.31 | 76 |
| ZZ | 2.91 | 0.19 | 1.83 | 0.13 | 2.50 | 0.17 | 7.25 | 0.46 | 35 |

FIG. 2B
MCDV DATA
Y = SUSCEPTIBLE
* = SIGNIFICANT AT .05 LEVEL   ** = SIGNIFICANT AT .01 LEVEL OR LOWER
REALLY COMBINED DATA -             - NO ESCAPES INCLUDED

B0815_B

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.17 | 0.20 | 1.92 | 0.14 | 2.62 | 0.18 | 7.72 | 0.49 | 31 |
| YZ | 3.03 | 0.12 | 1.87 | 0.08 | 2.43 | 0.11 | 7.33 | 0.29 | 87 |
| ZZ | 3.22 | 0.15 | 2.00 | 0.11 | 2.79 | 0.14 | 8.01 | 0.37 | 54 |

N0446_D

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.24 | 0.15 | 2.06 | 0.11 | 2.71 | 0.14 | 8.01 | 0.37 | 51 |
| YZ | 3.20 | 0.13 | 1.94 | 0.09 | 2.64 | 0.12 | 7.78 | 0.32 | 71 |
| ZZ | 2.82 | 0.18 | 1.67 | 0.13 | 2.28 | 0.16 | 6.77 | 0.43 | 38 |

U0050_A

| GENOTYPE | VEINB* MEAN | STD ERR | TWIST_T* MEAN | STD ERR | CHLOR** MEAN | STD ERR | CUM* MEAN | STD ERR | N |
|---|---|---|---|---|---|---|---|---|---|
| YY | 3.44 | 0.18 | 2.13 | 0.12 | 3.00 | 0.16 | 8.57 | 0.43 | 39 |
| YZ | 3.10 | 0.13 | 1.98 | 0.09 | 2.64 | 0.11 | 7.73 | 0.31 | 77 |
| ZZ | 2.72 | 0.19 | 1.68 | 0.13 | 2.26 | 0.17 | 6.66 | 0.46 | 35 |

N0296_D

| GENOTYPE | VEINB MEAN | STD ERR | TWIST_T** MEAN | STD ERR | CHLOR* MEAN | STD ERR | CUM* MEAN | STD ERR | N |
|---|---|---|---|---|---|---|---|---|---|
| YY | 3.42 | 0.18 | 2.21 | 0.11 | 2.91 | 0.16 | 8.54 | 0.42 | 38 |
| YZ | 2.92 | 0.13 | 1.70 | 0.08 | 2.36 | 0.11 | 6.98 | 0.30 | 76 |
| ZZ | 3.05 | 0.21 | 1.83 | 0.14 | 2.56 | 0.19 | 7.45 | 0.51 | 26 |

U0060_E

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.01 | 0.20 | 1.84 | 0.15 | 2.44 | 0.19 | 7.29 | 0.50 | 29 |
| YZ | 3.21 | 0.14 | 2.03 | 0.10 | 2.71 | 0.12 | 7.94 | 0.34 | 65 |
| ZZ | 2.93 | 0.20 | 1.81 | 0.14 | 2.40 | 0.18 | 7.14 | 0.50 | 30 |

N0386_A

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.36 | 0.20 | 1.82 | 0.14 | 2.82 | 0.16 | 7.99 | 0.49 | 29 |
| YZ | 3.03 | 0.12 | 1.94 | 0.09 | 2.47 | 0.11 | 7.44 | 0.31 | 72 |
| ZZ | 3.38 | 0.18 | 2.01 | 0.13 | 2.78 | 0.16 | 8.17 | 0.44 | 35 |

U0042_E

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 2.96 | 0.17 | 1.78 | 0.12 | 2.46 | 0.16 | 7.20 | 0.43 | 41 |
| YZ | 3.00 | 0.12 | 1.94 | 0.08 | 2.56 | 0.11 | 7.50 | 0.30 | 85 |
| ZZ | 3.51 | 0.20 | 2.05 | 0.14 | 2.97 | 0.18 | 8.53 | 0.48 | 32 |

N0396_B

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 2.94 | 0.18 | 1.71 | 0.13 | 2.42 | 0.17 | 7.07 | 0.44 | 37 |
| YZ | 3.09 | 0.11 | 1.96 | 0.08 | 2.57 | 0.10 | 7.62 | 0.27 | 101 |
| ZZ | 3.44 | 0.18 | 2.03 | 0.13 | 2.84 | 0.17 | 8.31 | 0.44 | 37 |

U0066_A

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 2.93 | 0.16 | 1.75 | 0.11 | 2.45 | 0.14 | 7.13 | 0.39 | 51 |
| YZ | 3.16 | 0.12 | 2.04 | 0.09 | 2.72 | 0.11 | 7.91 | 0.31 | 82 |
| ZZ | 3.21 | 0.21 | 1.93 | 0.15 | 2.67 | 0.19 | 7.81 | 0.52 | 28 |

U0019_D

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 2.95 | 0.16 | 1.74 | 0.11 | 2.39 | 0.14 | 7.08 | 0.39 | 47 |
| YZ | 3.11 | 0.13 | 1.98 | 0.09 | 2.58 | 0.11 | 7.67 | 0.31 | 73 |
| ZZ | 3.39 | 0.18 | 2.03 | 0.13 | 2.76 | 0.16 | 8.18 | 0.45 | 36 |

U0127_E

| GENOTYPE | VEINB* MEAN | STD ERR | TWIST_T* MEAN | STD ERR | CHLOR* MEAN | STD ERR | CUM* MEAN | STD ERR | N |
|---|---|---|---|---|---|---|---|---|---|
| YY | 2.77 | 0.16 | 1.72 | 0.11 | 2.28 | 0.14 | 6.78 | 0.39 | 47 |
| YZ | 3.37 | 0.15 | 2.17 | 0.11 | 2.86 | 0.14 | 8.40 | 0.37 | 52 |
| ZZ | 3.19 | 0.32 | 1.86 | 0.22 | 2.56 | 0.29 | 7.61 | 0.78 | 12 |

FIG. 2C

MCDV DATA

Y = SUSCEPTIBLE

* = SIGNIFICANT AT .05 LEVEL      ** = SIGNIFICANT AT .01 LEVEL OR LOWER

REALLY COMBINED DATA -                    - NO ESCAPES INCLUDED

B0571_B

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.14 | 0.20 | 1.91 | 0.14 | 2.71 | 0.19 | 7.77 | 0.50 | 30 |
| YZ | 3.18 | 0.11 | 1.97 | 0.08 | 2.69 | 0.11 | 7.85 | 0.28 | 94 |
| ZZ | 2.39 | 0.20 | 1.82 | 0.14 | 2.39 | 0.18 | 7.14 | 0.49 | 32 |

U0054_C

| GENOTYPE | VEINB* MEAN | STD ERR | TWIST_T MEAN | STD ERR | CHLOR** MEAN | STD ERR | CUM* MEAN | STD ERR | N |
|---|---|---|---|---|---|---|---|---|---|
| YY | 3.40 | 0.17 | 2.16 | 0.12 | 3.00 | 0.16 | 8.56 | 0.42 | 41 |
| YZ | 3.15 | 0.12 | 1.89 | 0.09 | 2.62 | 0.11 | 7.66 | 0.30 | 83 |
| ZZ | 2.62 | 0.20 | 1.79 | 0.14 | 2.19 | 0.18 | 6.60 | 0.49 | 31 |

U0126_A

| GENOTYPE | VEINB** MEAN | STD ERR | TWIST_T* MEAN | STD ERR | CHLOR** MEAN | STD ERR | CUM** MEAN | STD ERR | N |
|---|---|---|---|---|---|---|---|---|---|
| YY | 3.46 | 0.19 | 2.27 | 0.13 | 3.02 | 0.17 | 8.76 | 0.47 | 34 |
| YZ | 3.20 | 0.12 | 1.92 | 0.08 | 2.69 | 0.11 | 7.82 | 0.30 | 83 |
| ZZ | 2.63 | 0.18 | 1.75 | 0.13 | 2.21 | 0.16 | 6.60 | 0.44 | 38 |

N0239_A

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.32 | 0.16 | 2.11 | 0.11 | 2.70 | 0.14 | 8.13 | 0.38 | 50 |
| YZ | 3.19 | 0.12 | 1.94 | 0.09 | 2.63 | 0.11 | 7.75 | 0.30 | 79 |
| ZZ | 2.97 | 0.25 | 1.68 | 0.17 | 2.48 | 0.22 | 7.13 | 0.60 | 20 |

U0108_E

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.22 | 0.21 | 2.14 | 0.15 | 2.77 | 0.20 | 8.13 | 0.53 | 26 |
| YZ | 3.28 | 0.12 | 1.98 | 0.08 | 2.73 | 0.11 | 8.00 | 0.29 | 87 |
| ZZ | 2.90 | 0.21 | 1.79 | 0.15 | 2.38 | 0.19 | 7.07 | 0.52 | 27 |

B1428_E

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 2.97 | 0.18 | 1.79 | 0.12 | 2.37 | 0.16 | 7.14 | 0.44 | 39 |
| YZ | 3.08 | 0.14 | 1.92 | 0.09 | 2.64 | 0.12 | 7.64 | 0.34 | 68 |
| ZZ | 3.23 | 0.15 | 2.03 | 0.11 | 2.82 | 0.14 | 8.07 | 0.38 | 53 |

B0304_A

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.13 | 0.18 | 1.95 | 0.12 | 2.70 | 0.16 | 7.79 | 0.43 | 44 |
| YZ | 3.00 | 0.15 | 1.89 | 0.10 | 2.46 | 0.14 | 7.36 | 0.37 | 61 |
| ZZ | 3.16 | 0.20 | 2.00 | 0.13 | 2.68 | 0.18 | 7.83 | 0.48 | 36 |

N0264_A

| GENOTYPE | VEINB** MEAN | STD ERR | TWIST_T** MEAN | STD ERR | CHLOR** MEAN | STD ERR | CUM** MEAN | STD ERR | N |
|---|---|---|---|---|---|---|---|---|---|
| YY | 3.63 | 0.16 | 2.17 | 0.12 | 3.07 | 0.15 | 8.87 | 0.40 | 40 |
| YZ | 3.26 | 0.11 | 2.02 | 0.08 | 2.72 | 0.10 | 8.00 | 0.28 | 82 |
| ZZ | 2.54 | 0.15 | 1.59 | 0.11 | 2.03 | 0.13 | 6.16 | 0.36 | 49 |

U0064_B

| GENOTYPE | VEINB* MEAN | STD ERR | TWIST_T** MEAN | STD ERR | CHLOR* MEAN | STD ERR | CUM** MEAN | STD ERR | N |
|---|---|---|---|---|---|---|---|---|---|
| YY | 3.58 | 0.20 | 2.29 | 0.14 | 3.07 | 0.18 | 8.93 | 0.42 | 30 |
| YZ | 3.16 | 0.11 | 1.94 | 0.08 | 2.68 | 0.11 | 7.77 | 0.28 | 88 |
| ZZ | 2.81 | 0.18 | 1.66 | 0.13 | 2.30 | 0.17 | 6.77 | 0.46 | 34 |

N0445_B

| GENOTYPE | VEINB** MEAN | STD ERR | TWIST_T* MEAN | STD ERR | CHLOR** MEAN | STD ERR | CUM** MEAN | STD ERR | N |
|---|---|---|---|---|---|---|---|---|---|
| YY | 3.56 | 0.17 | 2.16 | 0.12 | 2.98 | 0.15 | 8.71 | 0.41 | 42 |
| YZ | 3.07 | 0.12 | 1.87 | 0.08 | 2.54 | 0.11 | 7.48 | 0.28 | 87 |
| ZZ | 2.81 | 0.16 | 1.76 | 0.11 | 2.30 | 0.14 | 6.87 | 0.38 | 48 |

N0285_E

| GENOTYPE | VEINB MEAN | STD ERR | TWIST_T MEAN | STD ERR | CHLOR* MEAN | STD ERR | CUM MEAN | STD ERR | N |
|---|---|---|---|---|---|---|---|---|---|
| YY | 3.52 | 0.19 | 2.07 | 0.13 | 3.09 | 0.17 | 8.68 | 0.47 | 30 |
| YZ | 3.14 | 0.13 | 1.84 | 0.09 | 2.53 | 0.11 | 7.50 | 0.31 | 69 |
| ZZ | 3.02 | 0.20 | 1.87 | 0.14 | 2.54 | 0.18 | 7.44 | 0.48 | 29 |

FIG. 2D

MCDV DATA

Y = SUSCEPTIBLE

\* = SIGNIFICANT AT .05 LEVEL    \*\* = SIGNIFICANT AT .01 LEVEL OR LOWER

REALLY COMBINED DATA -          - NO ESCAPES INCLUDED

B1428_E

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.30 | 0.15 | 1.97 | 0.10 | 2.59 | 0.13 | 7.86 | 0.36 | 54 |
| YZ | 3.48 | 0.11 | 2.09 | 0.07 | 2.75 | 0.09 | 8.32 | 0.25 | 108 |
| ZZ | 3.40 | 0.13 | 2.10 | 0.08 | 2.86 | 0.11 | 8.36 | 0.30 | 75 |

80304_A

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.28 | 0.16 | 2.02 | 0.10 | 2.75 | 0.14 | 8.05 | 0.38 | 51 |
| YZ | 3.41 | 0.11 | 2.07 | 0.07 | 2.66 | 0.09 | 8.15 | 0.26 | 111 |
| ZZ | 3.56 | 0.16 | 2.18 | 0.10 | 2.86 | 0.13 | 8.60 | 0.37 | 53 |

N0264_A

| GENOTYPE | VEINB** MEAN | STD ERR | TWIST_T** MEAN | STD ERR | CHLOR** MEAN | STD ERR | CUM** MEAN | STD ERR | N |
|---|---|---|---|---|---|---|---|---|---|
| YY | 3.60 | 0.15 | 2.16 | 0.09 | 2.93 | 0.12 | 8.69 | 0.33 | 73 |
| YZ | 3.09 | 0.10 | 1.93 | 0.06 | 2.48 | 0.08 | 7.51 | 0.23 | 154 |
| ZZ | 2.78 | 0.15 | 1.71 | 0.09 | 2.15 | 0.12 | 6.64 | 0.34 | 69 |

U0064_B

| GENOTYPE | VEINB** MEAN | STD ERR | TWIST_T** MEAN | STD ERR | CHLOR** MEAN | STD ERR | CUM** MEAN | STD ERR | N |
|---|---|---|---|---|---|---|---|---|---|
| YY | 3.85 | 0.16 | 2.35 | 0.10 | 3.13 | 0.14 | 9.33 | 0.38 | 44 |
| YZ | 3.48 | 0.09 | 2.10 | 0.06 | 2.80 | 0.08 | 8.39 | 0.21 | 139 |
| ZZ | 3.04 | 0.16 | 1.79 | 0.10 | 2.42 | 0.14 | 7.24 | 0.38 | 44 |

N0445_B

| GENOTYPE | VEINB** MEAN | STD ERR | TWIST_T* MEAN | STD ERR | CHLOR** MEAN | STD ERR | CUM** MEAN | STD ERR | N |
|---|---|---|---|---|---|---|---|---|---|
| YY | 3.50 | 0.15 | 2.11 | 0.09 | 2.84 | 0.12 | 8.45 | 0.34 | 75 |
| YZ | 3.06 | 0.11 | 1.91 | 0.06 | 2.46 | 0.09 | 7.43 | 0.24 | 146 |
| ZZ | 2.83 | 0.15 | 1.78 | 0.09 | 2.25 | 0.12 | 6.86 | 0.34 | 74 |

N0285_E

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 3.24 | 0.16 | 2.00 | 0.10 | 2.68 | 0.13 | 7.92 | 0.37 | 56 |
| YZ | 3.23 | 0.13 | 1.90 | 0.08 | 2.58 | 0.11 | 7.72 | 0.31 | 81 |
| ZZ | 3.20 | 0.19 | 1.94 | 0.11 | 2.61 | 0.16 | 7.75 | 0.44 | 41 |

N0306_B

| GENOTYPE | VEINB* MEAN | STD ERR | TWIST_T MEAN | STD ERR | CHLOR MEAN | STD ERR | CUM MEAN | STD ERR | N |
|---|---|---|---|---|---|---|---|---|---|
| YY | 2.93 | 0.23 | 1.89 | 0.14 | 2.35 | 0.19 | 7.17 | 0.53 | 25 |
| YZ | 3.60 | 0.12 | 2.15 | 0.08 | 2.79 | 0.10 | 8.53 | 0.28 | 89 |
| ZZ | 3.29 | 0.21 | 1.91 | 0.13 | 2.57 | 0.17 | 7.77 | 0.49 | 30 |

B1013_E

| GENOTYPE | VEINB MEAN | STD ERR | TWIST_T MEAN | STD ERR | CHLOR MEAN | STD ERR | CUM MEAN | STD ERR | N |
|---|---|---|---|---|---|---|---|---|---|
| YY | 2.40 | 0.56 | 1.93 | 0.37 | 2.00 | 0.49 | 6.33 | 1.35 | 5 |
| YZ | 2.75 | 0.29 | 1.77 | 0.19 | 2.28 | 0.25 | 6.81 | 0.69 | 19 |
| ZZ | 2.51 | 0.35 | 1.72 | 0.23 | 2.15 | 0.30 | 6.39 | 0.84 | 13 |

U0044_A

| GENOTYPE | VEINB MEAN | STD ERR | TWIST_T* MEAN | STD ERR | CHLOR MEAN | STD ERR | CUM MEAN | STD ERR | N |
|---|---|---|---|---|---|---|---|---|---|
| YY | 3.81 | 0.20 | 2.41 | 0.13 | 3.06 | 0.17 | 9.28 | 0.47 | 32 |
| YZ | 3.32 | 0.09 | 2.03 | 0.06 | 2.70 | 0.80 | 8.06 | 0.22 | 144 |
| ZZ | 3.39 | 0.16 | 2.03 | 0.10 | 2.69 | 0.14 | 8.11 | 0.38 | 49 |

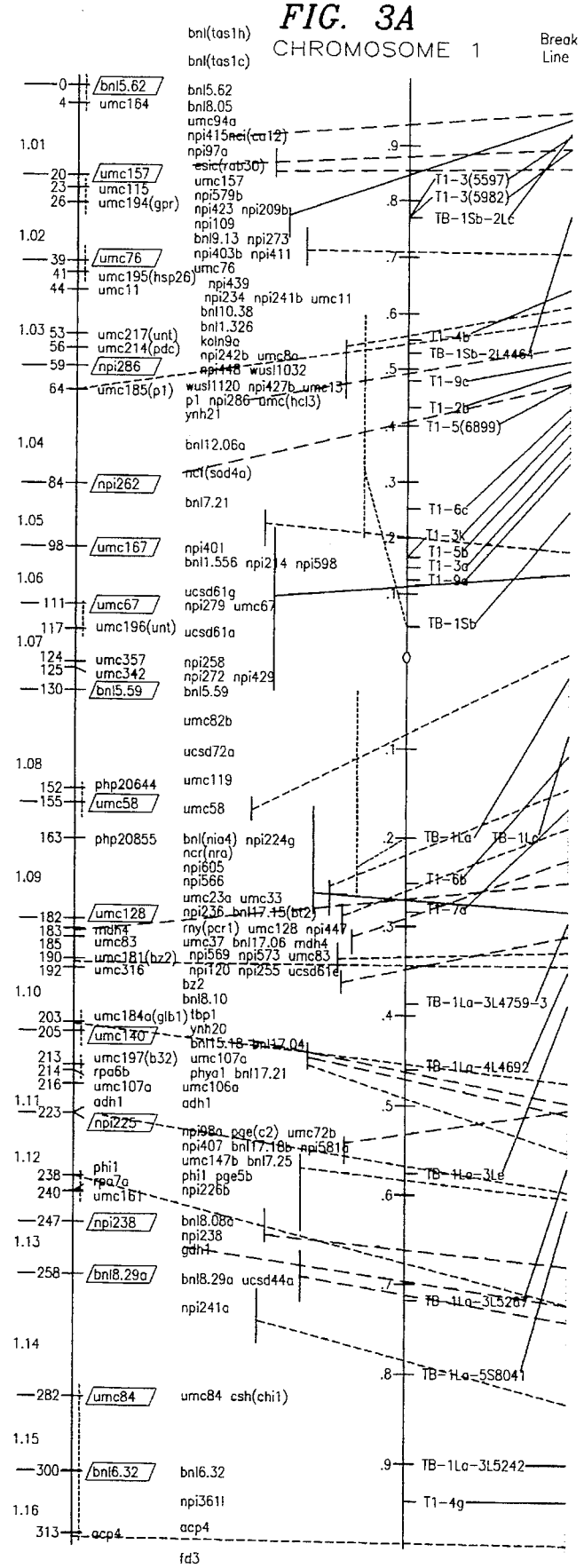
FIG. 3A CHROMOSOME 1

CHROMOSOME 1 CONT.

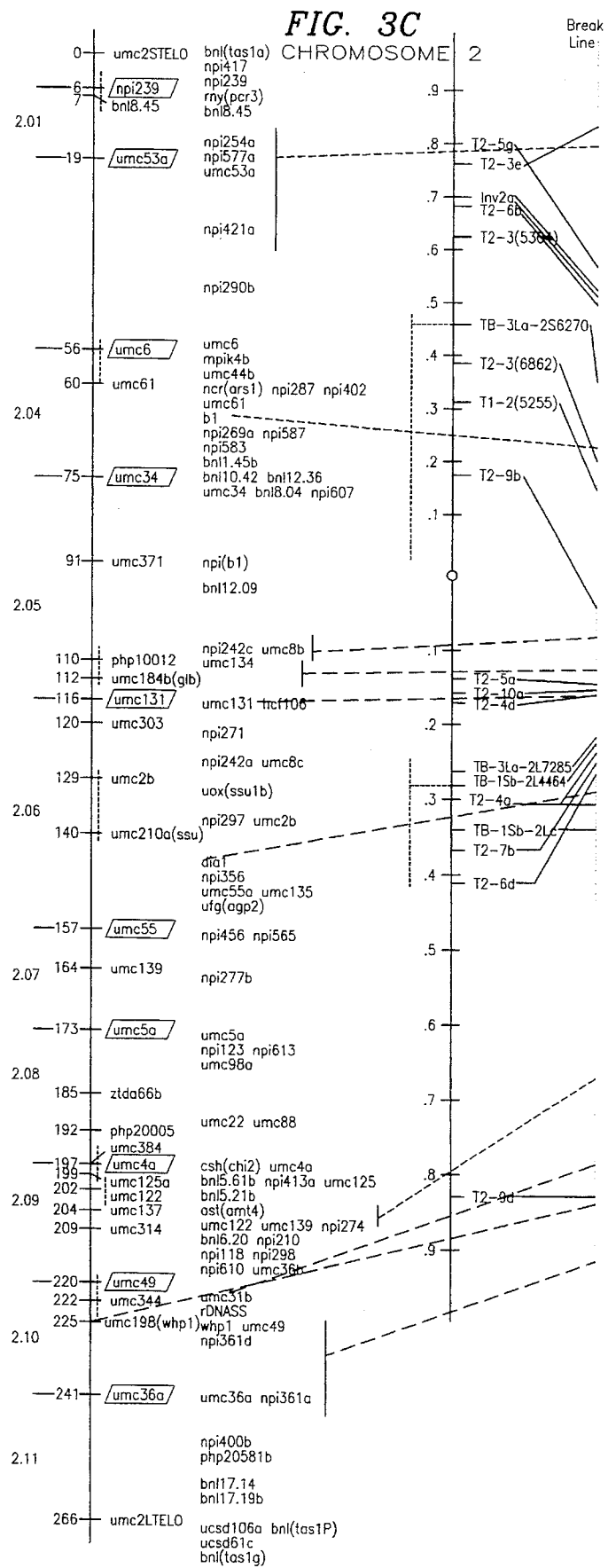
FIG. 3C CHROMOSOME 2

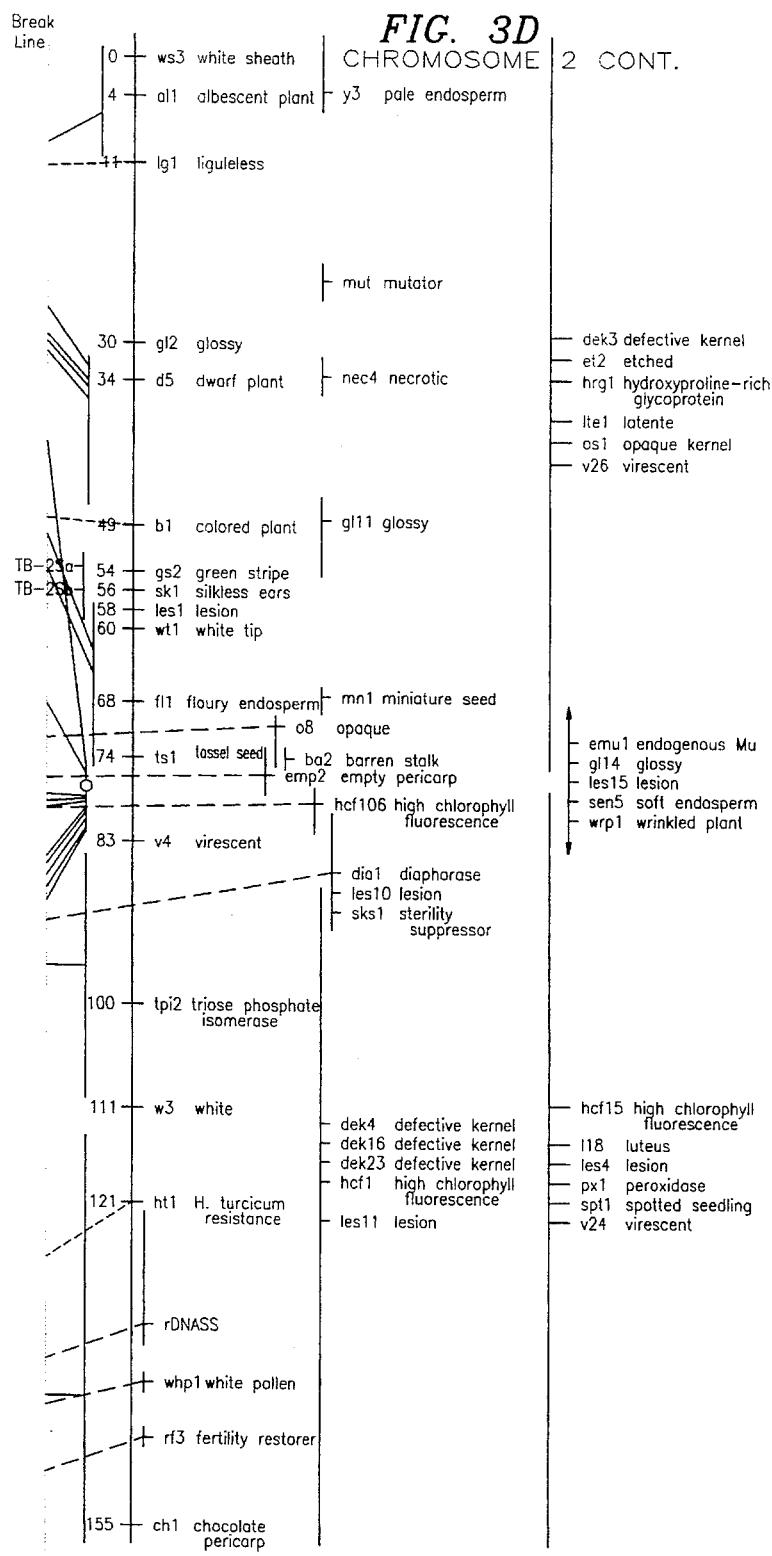
FIG. 3D CHROMOSOME 2 CONT.

CHROMOSOME 3

CHROMOSOME 3 CONT.

CHROMOSOME 4

CHROMOSOME 4 CONT.

CHROMOSOME 5

CHROMOSOME 5 CONT.

CHROMOSOME 6

CHROMOSOME 6 CONT.

CHROMOSOME 7 CONT.

CHROMOSOME 8

CHROMOSOME 8 CONT.

CHROMOSOME 9

CHROMOSOME 9 CONT.

CHROMOSOME 10

CHROMOSOME 10 CONT.

FIG. 4

```
           N214          N272      U33  U37
   N415   N234   U67  B559   N566  N447       B151B  N581A        B632
 1 ─────────────┤━━━━━━├──────────────────────────────────────────────
                  MCDV1

N446  1235  U102                                  N451
         B835  U50  U10   1135   N296       N432     N425A
 3 ─────────────┤━━━━━━━━├───────────────────────────────────────────
                   MCDV2

B436      N562  U54
   N579A     U40    N295    U126    N442 N288
 5 ──────────────────────────┤━━├─────────────────────────────────────
                              MCDV3

N112  U110  N389    N263
          B1540  U116  N455 U56 N283  N240    B1606    U35
 7 ──────────────────┤━━━━━━━├───────────────────────────────────────
                      MCDV4

B304              N455    N264   N563   U57A    B1013
10 ────────────────────────┤━━━━━━├──────────────────────────────────
                             MCDV5
```

MAIZE CHLOROTIC DWARF VIRUS RESISTANT MAIZE AND THE PRODUCTION THEREOF

This application is a continuation-in-part of U.S. patent application Ser. No. 08/235,028 filed on Apr. 28, 1994 now abandoned.

This invention relates to a maize plant and a method of producing same, which is resistant (which is defined as a plant having only mild symptomatic response) to Maize Chlorotic Dwarf Virus which will hereinafter be referred to simply as MCDV. More particularly this invention relates to introgression in maize of genetic material capable of causing the plant to be resistant to MCDV. Additionally the present invention relates to a method of introgression of the desired genetic material from one or more parent plants into the progeny with precision and accuracy.

BACKGROUND

Historically maize (corn) has been used as a source of food for human and animal consumption. Even today maize supplies about twenty percent of the world's calories. Any maize disease that is prevalent in a large range of the maize growing regions can have a substantial impact on the quantity of maize annually available for consumption. Thus disease resistant maize is understandably of great public interest. And likewise is the subject of particular interest in many corn breeding programs.

To date disease resistant maize has been developed by traditional breeding methods; unfortunately, there is usually a trade off between desirable agronomic traits and disease resistant plants. In fact, it is quite common to see poor agronomic traits associated with moving disease or insect resistance traits (genes) especially when the resistance is moved from unadapted germplasm into adapted germplasm. Rarely can disease resistant maize having agronomically desirable traits such as high yield in the hybrid combination be achieved by traditional plant breeding. One example of a disease resistant plant that has not yet been developed by traditional breeding is a MCDV resistant corn.

There is a need for MCDV resistant corn because plant damage from MCDV is found in a number of corn growing regions. Certain sections of these regions are more prone to crop loss from MCDV than are other regions. In corn plants damage from MCDV may result in yield decrease, plant loss, or failure to develop ears.

MCDV is transmitted in nature by an insect. The insect is a leafhopper, *Graminella nigrifrons* (Forbes). MCDV occurs where the leafhopper, its vector, and the virus' over-wintering host johnsongrass (*Sorghum halapense*) are located. At the beginning of the growing season the leafhoppers acquire the virus from infected johnsongrass and transmit it to the corn as the insects move about the field. An infected corn plant is identifiable because the virus causes certain characteristic symptoms including, but not limited to, veinbanding, leaf twisting, leaf margin tearing, and chlorosis of the whorl.

Traditionally there have been two principle ways of controlling MCDV, one is the rotation with soybeans, and the second is johnsongrass management. There is a need for the development of a virus resistant plant effective to control MCDV. The biggest problem with developing MCDV resistance has been with disease escapes, which are a function of insect behavior and whether or not they are viruliferous.

Additionally, under field conditions it has been difficult to positively diagnose this particular virus disease based on symptom expression. Controlled greenhouse screens have been undertaken to: (1) insure infection of a plant with the virus; and (2) evaluate the response of maize to the infection.

A screening procedure for the detection of resistance to MCDV permits inbred lines to be evaluated under freedom of choice conditions by the vector but in the absence of Maize Dwarf Mosaic Virus (MDMV) (which can evidence similar symptoms). *Graminella nigrifrons* adult leafhoppers are used as vectors of MCDV. These vectors acquire the virus by exposure to infected corn and then are released in intervals into a cage containing the seedling corn plants. The original leafhoppers are not removed even though two newly acquired groups of leafhoppers are added to the cage at timed intervals. This (multiple inoculation method) effectively infects the corn seedlings so their MCDV response can be rated.

Hitherto, few, if any, agronomically desirable varieties of corn having resistance to MCDV and also the necessary agronomic traits for commercial production have been produced. Some moderately tolerant sources are known but the genetic background of these frequently evidence agronomically undesirable characteristics. Given that pursuant to this invention it has been discovered that a large number of genes control both mild symptomatic response to MCDV, a progeny plant containing the desired mix of agronomic traits and MCDV resistant genes within its genome is expected to be a very rare occurrence indeed.

One of the fundamental principles of maize breeding whether for disease resistance or otherwise, is the production of a hybrid having a desired mix of traits by the combination of two inbreds. To produce improved hybrids, there is an ongoing development of new inbreds. An inbred is a plant which has become homozygous at almost all loci. There are two primary germplasm sources for producing new inbreds. One source is germplasm that has been genetically engineered; the second source is an adapted or an unadapted germplasm. This invention relates to the use of unadapted germplasm and not to genetically engineered germplasm.

In a conventional breeding program, pedigree breeding and recurrent selection breeding methods are employed to develop new inbred lines with desired resistant traits. Maize breeding programs attempt to develop these inbred lines by self-pollinating plants and selecting the desirable plants from the populations. An inbred produces a uniform population of hybrid plants when crossed with a second homozygous line, i.e., inbred. Inbreds tend to have poor vigor and low yield; however, the progeny of an inbred cross usually evidences vigor. The progeny of a cross between two inbreds is often identified as an $F_1$ hybrid. The resultant $F_1$ hybrids which may be heterozygous at a number of loci, are evaluated to determine whether or not they show the resistant trait and agronomically important and desirable traits. Identification of desirable agronomic traits has typically been done by breeders' expertise. A plant breeder identifies a desired trait for the area in which his plants are to be grown and selects inbreds which appear to pass the desirable trait or traits on to the hybrid.

Conventional plant breeders rely on phenotypic traits of the inbreds for selection purposes. Modern plant breeding technology looks at the genotypic material (chromosomes) for plant breeding purposes. One method of looking at plant genotypes is to use Restriction Fragment Length Polymorphisms (RFLPs) which provide a method for identifying the chromosomal regions which affect the agronomic traits in the plant genome which the plant breeder is attempting to introgress into the inbred line for ultimate expression in the hybrid.

RFLPs can be used to identify chromosomal regions in maize which is a ten chromosome plant. Each chromosome has a short arm with a distal and proximal end and a long arm having a distal and proximal end. Between the short arm proximal end and long arm proximal end is a centromere. Each chromosome is made up of strands of the deoxyribonucleic acid (DNA) molecule which has a specific nucleic acid sequence. Selected restriction endonucleases will identify a specific base sequence and cleave the DNA molecule wherever this sequence occurs. The resultant cleaved portions are called restriction fragments. These restriction fragments can be separated by size by electrophoresis through agarose gels.

The DNA of two individual maize plants will differ in sequence at a variety of sites. Because of this difference, restriction endonucleases may cleave an individual's DNA at a different site or location than the other individual's DNA. A polymorphism in the length of restriction fragments is produced when the fragments of the two individuals have different lengths. A polymorphism is detected by placing the fragments on an agarose gel electrophoresis apparatus and allowing them to separate by size over distance. A southern blot is then used. The fragments of the DNA are physically transferred on to a membrane, then nucleic acid hybridization detects the sequences by hybridization of the single strand of DNA (probe) on the southern blot. The nucleic acid reforms double stranded DNA. A radiolabelled probe is used to detect a particular (DNA) sequence. One method is to use a labelled probe such that the DNA fragment will be identifiable through autoradiography techniques.

A variety of maize genes have been mapped and identified using RFLPs. Certain polymorphisms (molecular markers) are used to identify chromosomal areas associated with certain traits. A large number of molecular markers including RFLPs have been applied to the maize genome and a detailed maize genetic linkage map that can be used to localize important genes has been constructed.

A variety of traits have been identified by RFLPs; for example, P1 pericarp color has been linked to UMC185(P1) on the short arm of chromosome one of the maize plant. Probes BNL6.29 and UMC85 on chromosome six of the maize plant have been identified with Maize Dwarf Mosaic Virus (MDMV) strain A resistance in maize. Likewise, a variety of other traits have been genetically identified and placed on the maize genetic linkage map.

It would appear that once a desired trait is recognized and the chromosome region expressing that trait is located between flanking probes in a maize plant by the use of RFLPs, that the trait should be readily introgressed into an inbred line. Unfortunately, it is not easy to recognize the desired gene location and although RFLPs are a tool which can be employed to help identify the chromosomal region to which the trait appears to be linked, RFLPs are not a solution in and of themselves. RFLPs are simply a tool of identification. It should be noted that the chromosomal regions associated with MCD resistance have not been identified or mapped using probes.

Because of the difficulties with working with the MCDV trait, almost nothing has hitherto been known about the genes responsible, for example, the number of genes involved, their action, and where they are located on the maize chromosomes. There is a need for the identification of the location of genes associated with resistance to MCDV which permit their tracking when introgressed into new plants through traditional breeding. There also remains a need for a method of transferring resistance to MCDV to a corn inbred that has desirable agronomic traits. There remains a need for MCDV-resistant inbreds and hybrids.

SUMMARY OF THE INVENTION

An object of the present invention is to provide a maize line which exhibits mild symptomatic response to MCDV without significant deterioration of the combining ability of inbred lines and the consequent loss of yield and other agronomically desirable traits in hybrid combinations.

A further object of the invention is to provide a commercially viable MCDV resistant hybrid.

Yet another object of the present invention is to provide a breeding method to identify and track chromosomal regions in plants which contain MCDV resistance.

Broadly then the present invention is an improved inbred maize line, being derived from a first parent which evidences a resistance to MCDV in hybrid combination and a second parent which evidences a susceptibility to MCDV and has elite germplasm with desirable yield and moisture characteristics in hybrid combination, and wherein the improved inbred line has the resistance to MCDV, in hybrid combination, not significantly less than that of the first parent in the same hybrid combination, and yield and moisture characteristics which are not significantly less than those of the second parent in the same hybrid combination.

Furthermore, the present invention includes an elite inbred maize plant, and parts thereof exhibiting resistance to MCDV, comprising a genome which is homozygous in respect to genes within identifiable chromosomal regions conferring resistance to MCDV and genes specifying desirable agronordic traits in hybrid combination, the genome being entirely of maize origin.

More specifically then the present invention encompasses a maize plant having resistance to MCDV, the genome of which contains genes associated with resistance to MCDV at one, or more than one locus selected from the group consisting of: (locus 1) chromosome 1, map units between 111 and 152; (locus 2) chromosome 3, map units 55 and 108; (locus 3) chromosome 5, map units 141 and 88; (locus 4) chromosome 7, map units 96 and 103; (locus 5) chromosome 10, map units 67 and 106; references to map units and chromosomal locations being references to the maize chromosome map published for the 1993 Maize Genetics Cooperation NewsLetter Mar. 15, 1993 at FIG. 3. The invention would include a plant which is homozygous at each of the loci numbered 1 to 5, and a plant in which the donor parent is selected from the group consisting of the corn line designated Mp705, progenitors thereof, resistant progeny thereof and resistant hybrids. It also encompasses an inbred maize line, designated ZS211MCDV having improved resistance to MCDV.

Additionally, the present invention is related to the production of hybrids using the converted inbreds or progeny of the converted inbreds. Thus the present invention includes a hybrid maize plant, or parts of the plant comprising the progeny of a cross between first and second inbred lines, at least one of the inbred lines being a converted line, genes conferring resistance to MCDV being present in the homozygous state in the genome of one or other or both of the first and second inbred lines such that the genomes of the first and second inbreds together donate to the hybrid a complement of genes necessary to confer the resistance to MCDV.

The present invention furthermore includes a method for the production of an inbred maize plant adapted for conferring, in hybrid combination with a suitable second inbred, resistance to MCDV. The method may include the steps of selecting a first donor parental line possessing the desired resistance and crossing same with an elite, high yielding second parental line to produce a segregating plant population. The method continues by screening the plant population for identified chromosomal loci of one or more genes associated with the resistance trait; selecting plants from the population having the identified chromosomal loci for further crossing and selection, and repeating the crossing and selection until a line is obtained which is homozygous for the resistance trait at the loci and has the necessary combining ability to give agronomically acceptable characteristics in hybrid combination.

The present invention includes specific combinations of alleles from both the donor parent (giving MCDV resistance) and the non-donor parent. The following recombined linkage blocks relate to specific inbreds. The donor being MP705 and the non-donor being either ZS211 or ZS053. Thus the arrangement of a recombination linkage block present on each of these chromosomes can be expressed as specific donors or as donor parent and non-donor parent generally. A recombined linkage block as present in chromosome 1 of the maize line ZS211MCDV, containing the arrangement of alleles ZS211:Mp705:ZS211 with crossovers proximate map units 111 and 152 the Mp705 insertion containing locus 1.

A recombined linkage block as present in chromosome 3 of the maize line ZS211MCDV, containing the arrangement of alleles ZS211:Mp705:ZS211 with crossovers proximate map units 55 and 108 the Mp705 insertion containing locus 2.

A recombined linkage block as present in chromosome 5 of the maize line ZS211MCDV, containing the arrangement of alleles ZS211:Mp705:ZS211 with crossovers proximate map units 141 and 88 the Mp705 insertion containing locus 3.

A recombined linkage block as present in chromosome 7 of the maize line ZS211MCDV, containing the arrangement of alleles ZS211:Mp705:ZS211 with crossovers proximate map units 96 and 103 the Mp705 insertion containing locus 4.

A recombined linkage block as present in chromosome 10 of the maize line ZS211MCDV, containing the arrangement of alleles ZS211:Mp705:ZS211 with crossovers proximate map units 67 and 106 the Mp705 insertion containing locus 5.

Another description of the broad invention is an improved first inbred maize line adapted to form a hybrid combination with a second inbred maize line, the improved first inbred maize line being derived from crossing a first parent having identifiable first parent chromosomal regions on selected chromosomes, and the second parent having identifiable second parent chromosomal regions on selected chromosomes, the first parent chromosomal regions having a trait conferring resistance to MCDV in hybrid combination, and a second parent having an agronomically desirable genotype in hybrid combination, except for the second parent's identifiable chromosomal regions on selected chromosomes, these second parent's chromosomal regions having a trait conferring relative sensitivity to MCDV wherein the improved inbred line derived from the first parent and the second parent has improved inbred line identifiable chromosomal regions on selected chromosomes which are substantially like the first parent chromosomal regions wherein the improved inbred line has the trait of resistance to MCDV, in hybrid combination, not significantly less than that of the first parent in the same hybrid combination, and has substantially all of the second parent's genotype except for the second parent's chromosomal regions having the trait conferring relative sensitivity to MCDV.

Still another description of an inbred of the present invention is an elite inbred maize plant, having resistance to MCDV, comprising: a genome, the genome being entirely of maize origin, which contains a genetic material having resistance to MCDV, the genetic material selectively introgressed into the elite inbred line, the selectively introgressed genetic material having resistance to MCDV being identifiable and located in specific chromosomal regions; and genetic material specifying high yield in hybrid combination.

The present invention includes a plant, which is homozygous for at least two of the chromosomal loci listed above. A plant converted to be resistant to MCDV in which an ancestor is the corn line designated Mp705 is clearly within the scope of the present invention. An inbred line which is homozygous for introgressed genes specifying MCDV resistance at all the loci 1–5 is likewise a part of the present inventions. The invention also covers hybrids. A Zea mays L. hybrid plant having improved resistance to MCDV, identifiable for at least two of the chromosomal loci 1–5, the hybrid being the result of a cross between an inbred maize line and the improved inbred maize line falls within the invention.

Also falling within the invention are any progeny derived from the germplasm having identifiable genetic material on at least some of the chromosomes 1,3,5,7,10 evidencing MCDV resistance. The invention is not limited to inbreds having all 5 loci. The invention includes complementary regions in two inbreds and the method of developing a hybrid therefrom. Thus a Zea mays L. hybrid plant, comprising the progeny of a cross between first and second inbred lines, genetic material conferring resistance to MCDV being present in the homozygous state in the genome of at least one of the first and second inbred lines such that the genomes of the first and second inbreds together donate to the hybrid a complement of genetic material necessary to confer the resistance to MCDV fits within the present invention. As does the method for the production of an inbred maize plant adapted to confer, in hybrid combination with a suitable second inbred, resistance to MCDV, comprising: selecting a first donor parental line possessing the desired MCDV resistance; crossing the donor line with a second inbred parental line, high yielding in hybrid combination, to produce a segregating population; screening the population for a member having on at least one of these chromosomes 1,3,5,7,10 genetic material associated with the resistance trait; selecting the member for further crossing and selection; and repeating the procedure until an inbred line is obtained which is homozygous for the resistance trait at the selected chromosome region.

Additionally the present invention encompasses the converted inbred lines and any resultant hybrids which were made pursuant to the use of the identified chromosomal regions. These inbred embodiments include at least the following inbreds ZS211MCDV, ZS053. Likewise the parts of the converted line are included, such as pollen and seed, or seeds and/or tissue.

A concise description of the method of the present invention is a method of producing a corn plant comprising: crossing a first parent corn plant with a second parent corn plant wherein one of the first and second parent corn plants is a converted inbred corn plant. The method above wherein the first and second parent corn plants are both converted corn plants. Additionally the following are within the present invention, a first generation ($F_1$) hybrid corn plant produced by crossing a first inbred female corn plant with a second inbred male corn plant, wherein the first or second parent corn plant is the converted inbred corn plant. Including the hybrid corn plant wherein the converted inbred corn plant is the female parent or the male parent. Finally the following method is within the present invention, a method for producing first generation ($F_1$) hybrid corn seed comprising crossing a first inbred parent corn plant with a second inbred parent corn plant, wherein the first or second parent corn plant is the converted inbred corn plant to produce first generation ($F_1$) hybrid corn seed, and first generation ($F_1$) hybrid corn plant produced by growing the hybrid corn seed.

BRIEF DESCRIPTION OF THE DRAWINGS

FIG. 1 is a table of data indicating the magnitude of statistical significance of the rating score differences of homozygous RFLP genotypes for each pair of adjacent RFLP probes;

FIG. 2 is a table of data developed for each probe site denoting the rating for each genotype of the progeny of a resistant Mp705 by susceptible Va35;

FIG. 4 is a map of probes to be used in association with FIG. 3 indicating where the specific probes and by reference to FIG. 3 the specific map units carrying MCDV resistance are located.

DETAILED DESCRIPTION OF THE EMBODIMENTS

Figure 3B:
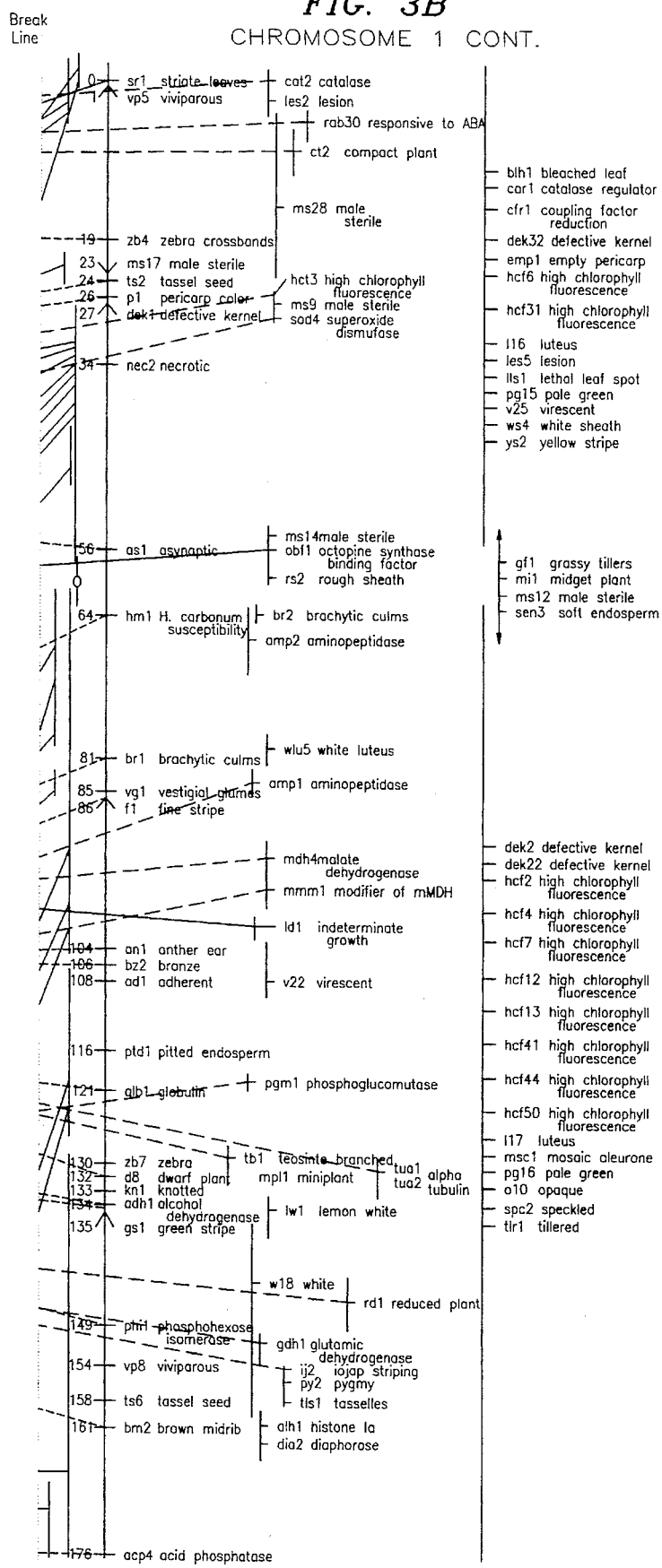
FIG. 3 is a map portion listing probes for the chromosomes of the maize plant. The map shown is from the map published by the 1993 Maize Genetics Cooperation News-Letter published Mar. 15, 1993, by Department of Agronomy and U.S. Department of Agriculture, University of Missouri, Columbia, Mo.

Broadly this invention relates to a maize plant and a method of producing same, which is resistant (which is defined as a plant having only mild symptomatic response) to Maize Chlorotic Dwarf Virus. This invention relates to introgression in maize of genetic material (for the first time identified) capable of causing the plant to be resistant to MCDV. Additionally the present invention relates to a method of introgression of the desired genetic material from one or more parent plants into the progeny with precision and accuracy. It will be appreciated that the MCDV converted line offers a much improved donor for use in pedigree or backcross breeding programs because recombination of genes for yield and other desirable agronomic traits and MCDV mild symptomatic response has already been accomplished by the present invention.

To assist in the description of this invention the following glossary of terms are provided.

Converted Plant—any plant having resistance to MCDV and additionally the plant or an ancestor of the plant having been selected by reference to RFLP data for at least one of the loci 1–5.

Crossover—shall mean an exchange of segments of homologous chromosomes during meiosis whereby linked genes become recombined; also the product of such an exchange. The cross-over frequency is the proportion of gametes bearing a cross-over between two specific gene loci. It generally ranges from 0 for allelic genes to 50% for genes so far apart that there is always a cross-over between them. The cross-over site is the place in the chromosome where breakage and reunion of DNA strands occur during recombination.

Introgression—shall mean the entry or introduction of a gene or a linkage block from one plant into another.

Introgressing—shall mean entering or introducing a gene or a linkage block from one plant into another.

Linkage Block—shall mean an identified chromosomal region containing genetic material that expresses a desired trait.

Recombination—shall mean reassortment of genes or characters in combinations different from what they were in the parents, in the case of linked genes by crossing over.

The method of the invention comprises the use of molecular markers to select progeny from a cross between an MCDV resistant donor and a high yielding, susceptible recipient whose progeny contain all or most of the preferred alleles for mild symptomatic response to MCDV and agronomically desirable traits. It is not necessary (or often inefficient) to find the complete complement amongst the progeny of a single cross. Rather, it is possible to select individual progeny plants exhibiting a proportion of the desired recombinations and to further cross or backcross such individuals in order to create the desired genome progressively.

The donor parent is preferably the line designated Mp705 or its progenitors or resistant progeny containing the loci 1–5 (described below) which are detectable by RFLP or equivalent molecular marker analysis. The donor of the MCDV resistant genetic material used in the present invention is the line designated Mp705. This is a public line. Other sources of this genetic material will of course be located since the present invention now allows this material to be identified.

The present invention has the entire yield/agronomic/ virus resistance package and includes a method using modern breeding techniques to move the desirable genetic material from elite backgrounds to other elite backgrounds or from germplasm source material to elite backgrounds, etc.

Historically disease assessment of MDCV infected plants has been based on incidence of infection. This type of assessment would not permit consistent differentiation of the response of maize inbreds and hybrids to inoculation with MCDV. Thus, a new assessment procedure assessed the disease based on symptom severity instead of the traditional disease incidence test. To develop this procedure controlled inoculation techniques were used in both the greenhouse and field experiments.

Disease assessments using visual ratings based on symptom severity (1 to 5 scale) of three leaf symptoms (veinbanding, twisting of the leaf and tearing of the leaf margin, and chlorosis of the whorl) and incidence of MDCV infection were used in attempts to classify the responses of maize genotypes. Symptom expression was amplified through controlled inoculation of seedlings with an isolate of MCDV that causes severe symptom expression (MCDV-S) in susceptible genotypes. The responses of field-grown plants to MCDV-S also were compared with responses to MCDV-T (type isolate).

The results of these controlled experiments found that a disease assessment procedure based on ratings of the severity of the three symptoms on a 1–5 scale, 3–4 weeks after inoculation clearly differentiated the inbreds and hybrids.

Thus, the newly developed disease assessment procedure was employed in an experiment designed to ascertain the degree of MCDV tolerance in characterized and uncharacterized maize germplasm using the severe isolate of MCDV (MCDV-S). An example of the experiment was as follows:

Evaluation of F2 Plants for Tolerance to MCDV-S

Method: Four hundred eighty seeds of $F_2$. (Va35 X Mp705) were planted (1 kernel/pot) and 80 pots of OH28 every two weeks for a total of three plantings. At 14 days of age 56 $F_2$ and 8 OH28 seedlings were placed in each of seven cages and 640 viruliferous *Graminella nigrifrous* leafhoppers (GNLH) were placed in each cage for a 48 hour IAP. Plants also were placed in an another cage without leafhoppers (LH). All plants were fumigated when they were removed from the cages and were placed on GH benches as batches of 72 plants (=52 inoc F2, 8 inoc OH28, 8 UNINOC F2). Each plant was identified by a stake, indicating ear number and plant number after plants were inoculated. Plants were rated (1–5 scale for VB, TT, WC) and measured weekly for four weeks.

Materials: 4480 leafhoppers to inoculate plants from each planting.

First planting on November 8:

| ENTRY | STAKE ID # | #K PTD | GERM | ID |
|---|---|---|---|---|
| Va35xMp705 | 1 | 160 | 133 | 8/5 C367-1x (270K Left) |
| " | 2 | 160 | 147 | 8/6 C367-7x (318K Left) |
| " | 3 | 160 | 120 | 8/6 C367-12x (370K Left) |
| Va35 | 4 | 24 | 22 | 8/12 881993-11x |
| Mp705 | 5 | 24 | 20 | 7/25 C361-1x |
| Va35x705 | 6 | 24 | 12 | 8/6 C279-3x C361-8 |
| Oh28 | 7 | 144 | 94 | |

In cages for initial access period IAP 11/22–24: (Used 10 leafhoppers per plant in cages 1–7)

| CAGE # | CONTENTS |
|---|---|
| 1 | 56 #1, 8 #7 |
| 2 | 56 #2, 8 #7 |
| 3 | 56 #3, 8 #7 |
| 4 | 56 #1, 8 #7 |
| 5 | 56 #2, 8 #7 |
| 6 | 56 #3, 8 #7 |
| 7 | 8 44, 45, 46, 47; 16 #1; 16 #2 |
| 8 | 8 #1, #2, #3, #4, #5; 4 #6; 20 #7 (No leafhoppers in this cage) |

This experiment employed a single inoculation of plants with the viruliferous leafhoppers. The results of this and similar experiments led to the first quantitative description of the tolerance to MCDV of an inbred Mp705 and to the susceptibility of Va35 to MCDV-S. The $F_2$ and $F_{2:3}$ Va35× Mp705 populations were screened using the single inoculation cage system and the 1–5 rating system. The DNA was extracted and the material was fingerprinted for possible chromosome regions. The fingerprinting was analyzed in light of the tolerance ratings and the preliminary molecular market data using Knapp & Bridges (1990) Th. App. Gen. 79:583–592 shown on the Chart 1.

Chart 1

LIKELIHOOD PROBABILITIES FOR QUANTITATIVE TRAIT LOCI SET #6 COMPARED TO ALL OTHER SETS
L1 = LIKELIHOOD PROBABILITY TESTING THE NULL HYPOTHESIS OF NO QTL EFFECT

| Chromosome # | Probes | SET #6 L1 | ALL OTHERS L1 |
|---|---|---|---|
| 1 | UMC76 & UMC13 | NO (0.27) | NO (0.34) |
| 1 | UMC13 & UMC119 | NO (0.79) | YES (0.008) |
| 1 | UMC119 & UMC67 | NO (0.81) | YES (0.003) |
| 1 | UMC67 & UMC33 | NO (0.14) | YES (0.03) |
| 1 | UMC33 & UMC107 | NO (0.29) | YES (0.02) |
| 1 | UMC107 & UMC84 | NO (0.17) | YES (0.000) |
| 2 | UMC53 & UMC34 | NO (0.86) | NO (0.16) |
| 2 | UMC34 & UMC6 | NO (0.63) | NO (0.48) |
| 2 | UMC6 & UMC139 | NO (0.19) | NO (0.76) |
| 2 | UMC139 & UMC49 | NO (0.32) | NO (0.81) |
| 2 | UMC49 & UMC36 | NO (0.39) | NO (0.37) |
| 3 | UMC50 & UMC26 | NO (0.66) | YES (0.04) |
| 3 | UMC26 & BNL15.2 | NO (0.33) | NO (—) |
| 3 | BNL15.2 & UMC63 | NO (0.48) | NO (0.08) |
| 3 | UMC63 & UMC96 | NO (0.91) | YES (0.05) |
| 4 | UMC31 & UMC42 | NO (0.36) | NO (0.21) |
| 4 | UMC42 & UMC66 | NO (0.42) | NO (0.22) |
| 4 | UMC66 & UMC52 | NO (0.44) | NO (0.12) |
| 4 | UMC52 & BNL8.23 | NO (0.87) | NO (0.13) |
| 5 | UMC72A & BNL5.02 | NO (0.23) | NO (0.80) |
| 5 | BNL5.02 & BNL5.71 | NO (0.86) | NO (0.89) |
| 5 | BNL5.71 & UMC126 | NO (0.29) | YES (0.02) |
| 5 | UMC126 & UMC54 | NO (0.32) | YES (0.01) |
| 5 | UMC54 & UMC104 | NO (0.57) | NO (0.16) |
| 6 | UMC85 & UMC65 | NO (0.85) | NO (0.08) |
| 6 | UMC65 & UMC21 | NO (0.85) | NO (0.68) |
| 6 | UMC21 & UMC138 | NO (0.91) | NO (0.62) |
| 6 | UMC138 & UMC71 | NO (0.36) | NO (0.69) |
| 6 | UMC71 & UMC28 | NO (0.39) | NO (0.14) |
| 7 | BNL15.40 & UMC116 | NO (0.45) | NO (0.11) |
| 7 | UMC116 & UMC110 | NO (0.20) | NO (0.15) |
| 7 | UMC110 & BNL14.07 | YES (0.04) | YES (0.04) |
| 7 | BNL14.07 & BNL16.06 | NO (0.06) | NO (0.86) |
| 8 | UMC103 & UMC124 | NO (0.49) | NO (0.15) |
| 8 | UMC124 & BNL9.44 | NO (0.50) | NO (0.39) |
| 8 | BNL9.44 & UMC89 | NO (0.31) | NO (0.08) |
| 8 | UMC89 & UMC48 | NO (0.95) | YES (0.03) |
| 8 | UMC48 & UMC7 | NO (0.20) | NO (0.10) |
| 9 | UMC95 & BNL14.28 | NO (0.40) | NO (0.22) |
| 10 | BNL3.04 & UMC64 | NO (0.07) | YES (0.02) |
| 10 | UMC64 & UMC44 | YES (0.05) | YES (0.009) |

This invention was further developed to produce tolerant maize plants in two stages. The first stage partially described above was the location of the chromosomal regions containing genes that characterize the plant as expressing mild symptomatic response to MCDV. The second stage was the introgression of the identified chromosomal regions into a genotype that has agronomically desirable traits.

The first stage required two things: a plant or plants that have the desired trait, in this case, expression of mild symptomatic response (MSR) to MCDV, and an accurate and reliable screening procedure to determine whether progeny of the MSR MCDV plants have the desired trait. A reliable screening procedure was developed at The Ohio State University, Ohio Agriculture Research Development Center by USDA/ARS and Ohio State University scientists. This procedure was used to confirm that the public line Mp705 has a MSR to MCDV. Mp705 was released to the public in Mississippi as a germplasm inbred. This type of a release indicates that this germplasm has sufficient deficiencies in overall agronomic characteristics that it is not elite material. In other words, it is not germplasm material which can be crossed with a second elite inbred and form a commercially acceptable hybrid, i.e. a hybrid with commercially acceptable agronomic traits. Furthermore, limited data on the desirable agronomic traits of Mp705 when in a hybrid combination further indicate the unacceptable agronomic characteristic.

In spite of its agronomically undesirable traits, Mp705 was discovered to have one very desirable trait. Mp705 expresses mild symptomatic response to the MCDV virus. To locate the chromosomal regions associated with the MSR to MCDV, the resistant plant Mp705 was crossed to Va35, a publicly available line released by Virginia Polytechnical Institute. The seed from the $F_1$ population was planted to form the segregating $F_2$ population. The $F_2$ population was screened by the following procedure to identify the degree of tolerance shown in the plant to MCDV.

*Graminella nigrifrons* adult leafhoppers were used as vectors of MCDV. The leafhoppers were reared continuously on oats and maize in 38×38×38 cm dacron-organdy-covered cages in a greenhouse rearing room facility at 25°±3° C., 50–70% RH, and 16 h light/day. The virus isolates used were obtained from maize trap plants exposed in southern Ohio in 1980 and confirmed by serology. To obtain inoculative vectors, the young adult leafhoppers were aspirated into 19×38×38 cm cages containing five (5) MCDV-infected inbred line Oh28 maize seedlings and allowed a 48 hour acquisition access period on these 35-day-old source plants. The leafhoppers were released in a transfer chamber and immediately aspirated into 91 cm square by 61 cm high inoculation cages covered with 32-mesh saran screen.

The problem of disease escapes was ameliorated and the affect of variability in a leafhopper transmission behavior was lessened by having a compact, multiple-inoculation method which exposed seedlings (2–3 days old) to a different group of viruliferous leafhoppers at two day intervals or for a 6 day period in a growth-chamber environment. MCDV infection was usually detected when the isolate (which has been called white striped by Hunt et al) was used because it causes severe vein banding, chlorosis and twisting and tearing of the leaves in susceptible maize.

In this highly effective screening procedure, a group of infective leafhoppers were selected and released into the saran screen cages containing the 14-day old test plants for an inoculation access period (Iap) of 48 hours in the greenhouse. A different group of viruliferous leafhoppers (640 leafhoppers each) was added to the test plants in a dacron-organdy-covered cage at each iap at two day intervals over a six day period in the growth chamber without first removing the previous batch of leafhoppers from the cage. The growth chamber was programmed to provide a photoperiod of 14:10 (Light:Dark) h (250 µE $m^{-2}s^{-1}$ photo flux density) with a 24:18° C. temperature, respectively. In this method, the seeds of the maize test plants were first surface-sterilized for 2–3 minutes with a 50:50 (vol/vol) solution of 95% ethyl alcohol and 0.05% sodium hypochlorite, rinsed with water, and blotted dry. Seeds were placed in petri dishes (9 cm) on five sheets of Thomas No 4704 H15 filter paper wetted with 10 ml tap water, then incubated in the dark at 30° C. for 30 hours. Germinated seeds, as indicated by an emerging radicle, were planted singly in 'Cone-Tainers' containing sterilized greenhouse soil and 0.2 gm of 14:14:14 slow release Osmocote fertilizer (Grace/Sierra, Milpitas, Calif.).

After the three inoculation access periods (Iap) at two a day intervals was completed there were 1,920 leafhoppers in the cage. Plants were fumigated with 1 ml vapona and transplanted. A single inoculation method was also employed during the development of the present invention.

In the second step of this screening procedure the disease severity assessment of the MCDV infected corn plants was determined based on visual readings of three symptoms on a 1 to 5 scale at three weeks after inoculation. 1 equals no symptoms and 5 equals severe symptoms. The symptom rating rates veinbanding (VB), twisting of the leaves and tearing of the leaf margin (TT,) chlorosis of the whorl (CH). The cumulative score of the rating of the symptoms gave a measure of the degree of symptomatic response. This response or tolerance ranges from mild to severe. Mild is a rating of the mean value of the combined symptom scores (VB) (Veinbanding); (TT) (Twisting & tearing); CH (chlorosis of the whorl) of 1–2.9. A mild tolerance score is defined as resistant. Non mild is any score above the mild score; the higher scores in the non mild range such as between 3.1 and 5.0 are classified as severe.

This screening procedure allowed the identification of the extreme tails of the $F_2$ populations. In other words, plants which were extremely susceptible and plants which were extremely resistant to MCDV were identified.

Then identification of the chromosomal regions associated with MSR to MCDV were located by the use of comparison of the RFLP data between the susceptible and resistant plants with the data rating the veinbanding (VB), the leaf twisting and tearing (TT), and the chlorosis of the whorl (CH) of the plants. Approximately 150–200 plants were used to generate the data shown in FIG. 1. The RFLP data shown in FIG. 1 was generated by the following RFLP protocol:

A. DNA Extraction

The corn plant tissue was lyophilized, ground to a fine powder in a mill and the DNA was extracted. 100 ml of RNase (10mg/ml) were placed in tubes and the supernate was filtered and placed in the tubes and incubated. The DNA precipitate was snagged, transferred to a culture containing 76% ETOH/10 mM $NH_4Ac$, and incubated. See Proc. Natl. Ac. Sci. USA 81:8014–8018

B. DNA Digestion

The DNA was quantified fluorimetrically, and digested to completion. DNA was loaded onto slab gel and electrophoresised. DNA was transferred onto Hybor-N+membrane (Amersham) via southern blotting. The protocol used is the protocol suggested by the manufacturer.

C. Southern Blotting

A matrix of Hybond $N^+$ Nucleic Acid transfer membrane, was soaked in 25 mM $NaH_2PO_4$ at –pH 6.5. The blots were baked for two hours. The Southern Blot procedure is well known in the art at J. Mol. Biol. 98:503 (1975).

D. Oligo Reaction 40 mg DNA was mixed with sufficient $H_2O$ to make up 3 ml of solution. The DNA was denatured for ten minutes at 95° C. and then 10 ml oligo buffer, 2 ml BSA, 5 ml 32P-dctp, 2 ml Klenow was added. These solutions are commercially available from Ceres and were mixed per manufacturer's instructions. The sample was incubated and then a 150 ml stop buffer was added. This protocol is published in Feinberg, A. P., B. Volgelstein, Anal. Biochem. 132:6, 1983.

E. Probe Hybridization

Probe fragments were generated from recombinant plasmids using PCR and the products gel-purified prior to labelling with 32p-ctp (Amersham) via random priming. The blots were decanted and placed on Kodak XAR X-ray film and exposed. The procedure used is published in B. Buddowle, et.al. Crime Laboratory Digest 15:3–21, 1988.

F. Probe Removal

The blots were washed in 5 mM Tris-HCL/pH 8.0, 0.2 mM EDTA 0.05% pyrophosphate, 0.1× Denhart's for 1–2 hours at 65°–75° C. Denhart's Solution –50× is formed as follows: Ficol - 5 g, polyvinylpyrolidone - 5 g, BSA (Pentax Fraction V)- 5 g, $H_2O$ - 500 ml. Then rinsed in 1×SSPE. SSPE (2××) is formed as follows: 174 g NaCl, 27.6 g $NaH_2PO_4$ $H_2$), 7.4 g EDTA, 800 ml $H_2O$, adjust pH 7.4, bring volume to 1 liter.

Two methods of statistical analysis were done with the data resulting from the above procedure, a locus-by-locus analysis of variance and an analysis using pairs of RFLP markers. The Statistical Analysis System (SAS) package of programs was used for data analyses. SAS is commercially available from: SAS Institute, Inc., SAS Campus Drive, Cary, N.C. 27513. The GLM procedure on SAS was run, by RFLP locus, for the means of three allelic classes: YY, YZ, and ZZ, designating homozygous RFLP marker alleles for one parent, heterozygous, and homozygous for the other parent. This analysis gives a probability of observing differences in average values for each of the three classes by chance, called the level of significance. In keeping with general scientific usage, significance levels less than 0.05 are denoted "statistically significant," and those less than 0.01 "highly significant," both indicating that the class averages are enough different to be unlikely to have arisen by chance. Results of these analyses are presented in FIG. 2 and Table 1.

The second analysis method uses pairs of adjacent RFLP markers to obtain a more precise estimate of statistical significance for additive genetic effects. The additive effects are defined as in "Introduction to Quantitive Genetics, Third Edition" by D. S. Falconer (1989, Longman Scientific and Technical) as half the difference in homozygous class means. The SAS procedure REG was used. The trait measurements were regressed on variables X1 defined as −1, 0, 1 for ZZ, YZ, YY respectively, for the first RFLP marker, and X2 coded similarly for the second marker. The sum of the regression coefficients for X1 and X2 then gives a good estimate of the additive genetic effect. Results of this analysis are in FIG. 1.

for the probe indicates derivation from the resistant (Mp705) plant). Results of the statistical analysis of the plant rating at each probe location based on the level of statistical significance, helped identify the chromosomal regions of interest. On chromosome one the U0067 probe had cumulative mean score for the YY (homozygous susceptible class) of 8.90 and a ZZ cumulative mean of 6.50. The difference is highly significant. The U0119 probe on chromosome one likewise is significant at the 0.01 level, having a YY mean of 8.67 and a ZZ mean of 6.49. Probes N0447, U0107, and U0084 on chromosome one also were highly significant.

Figure 3E:
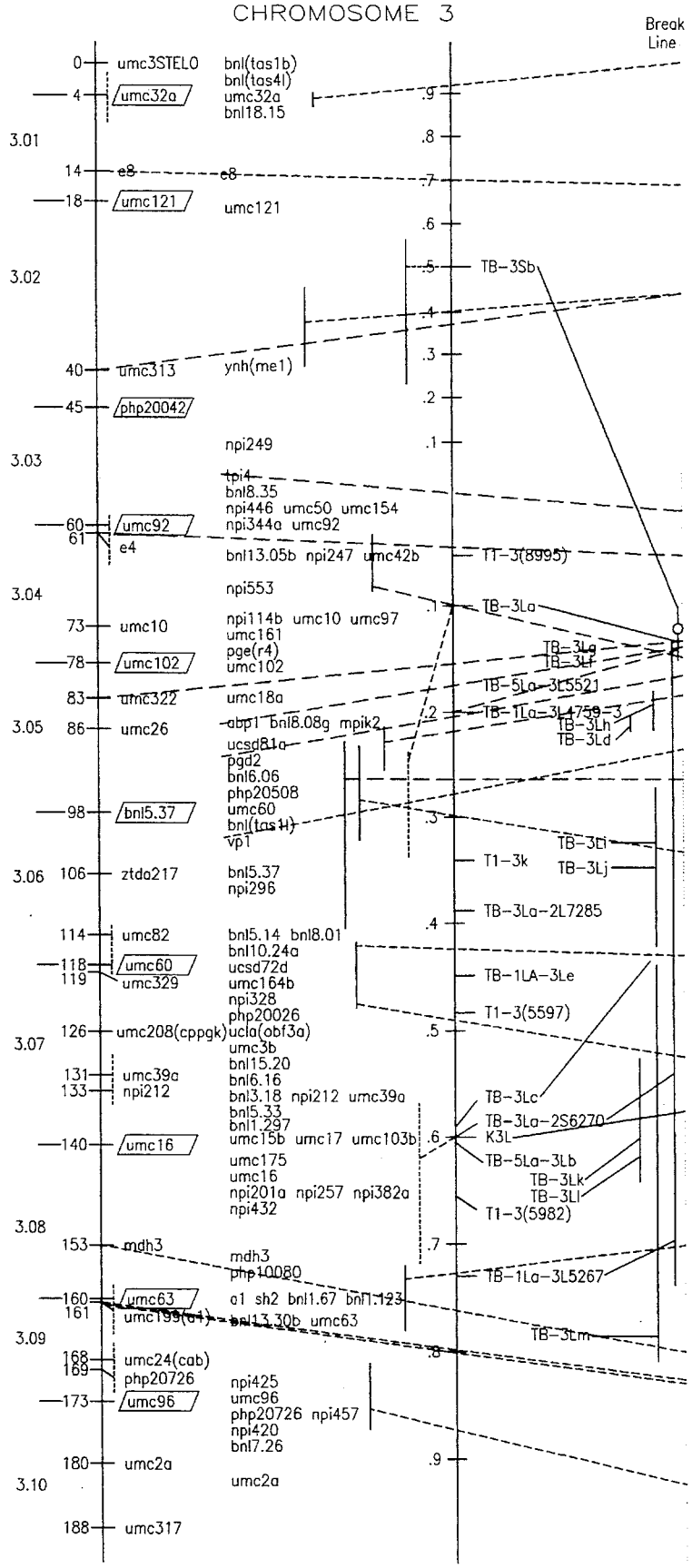
Figure 3F:
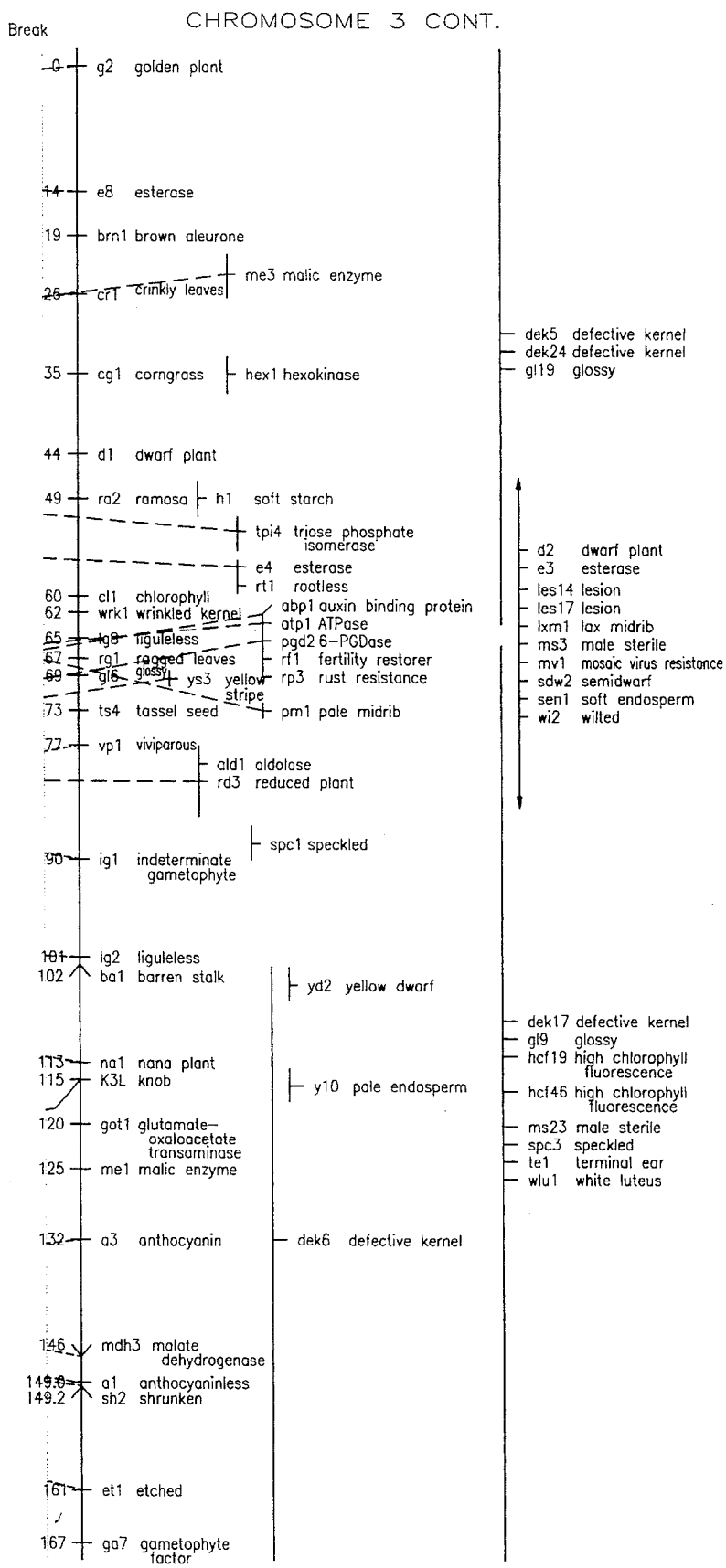
Figure 3G:
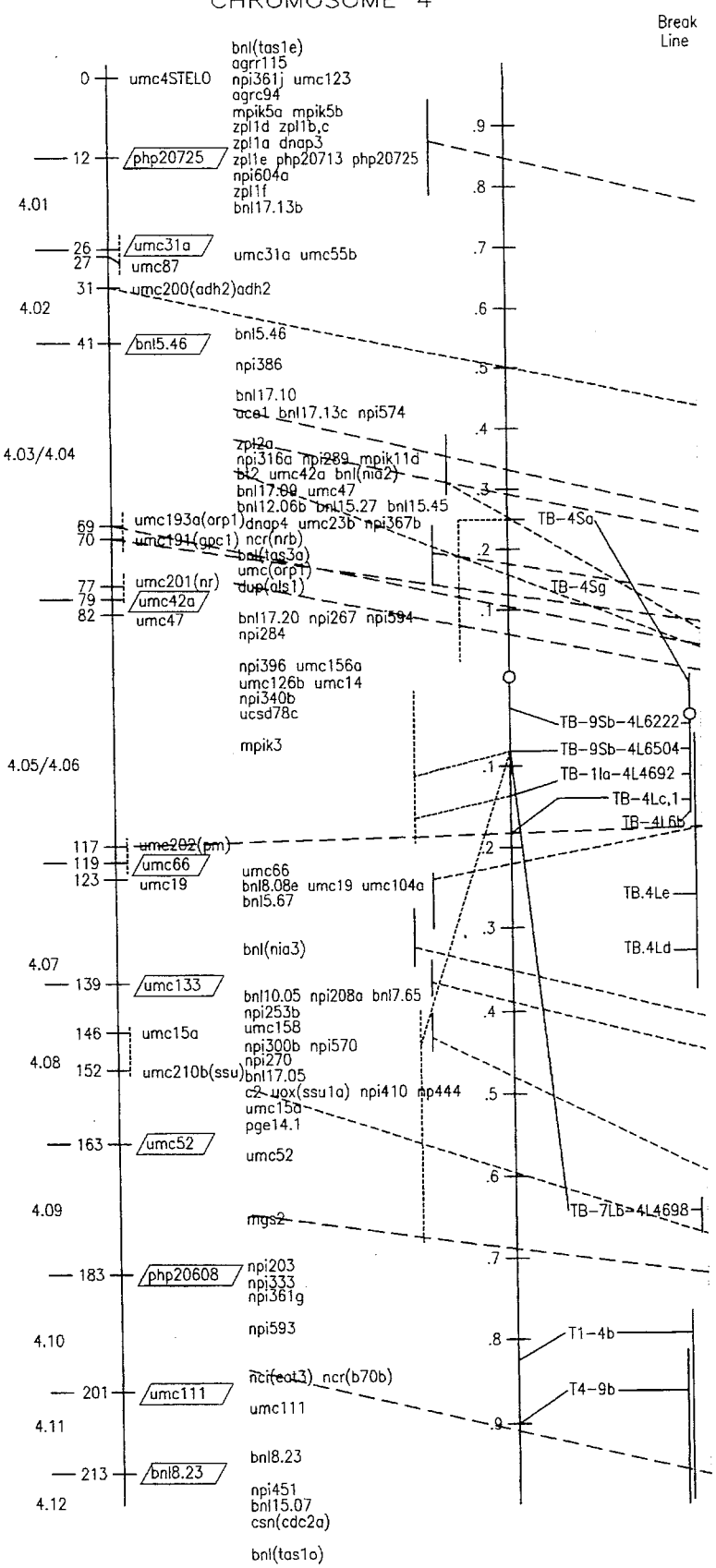
Figure 3H:
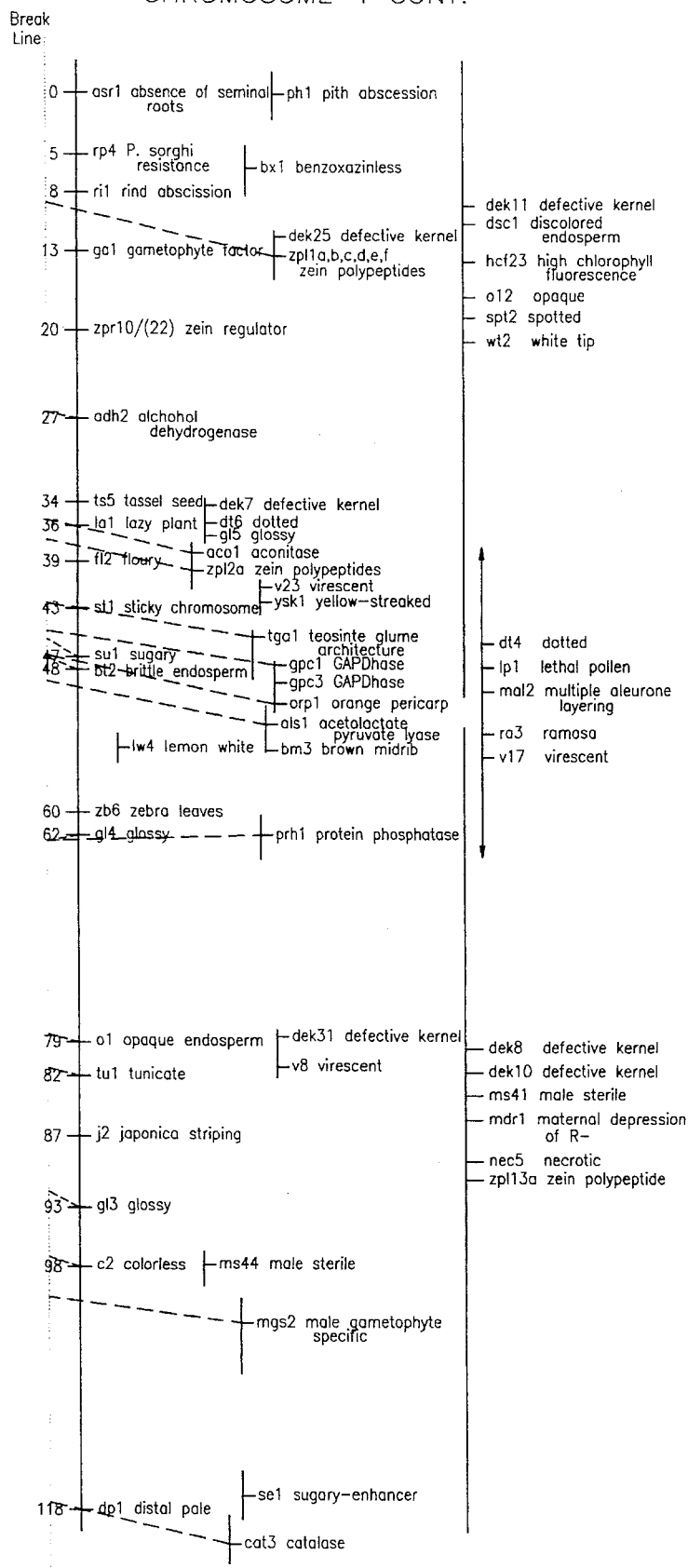
Figure 31:
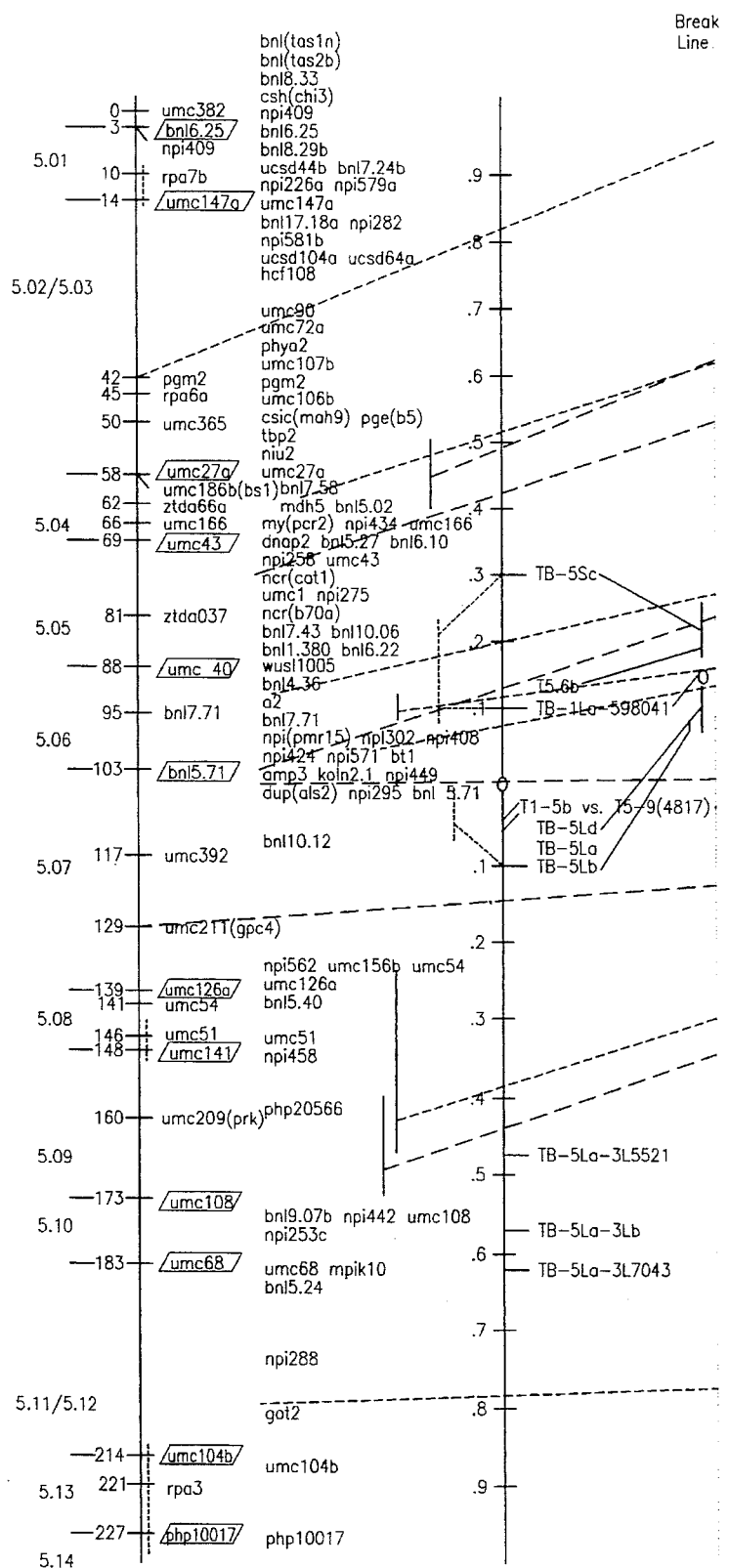
Figure 3J:
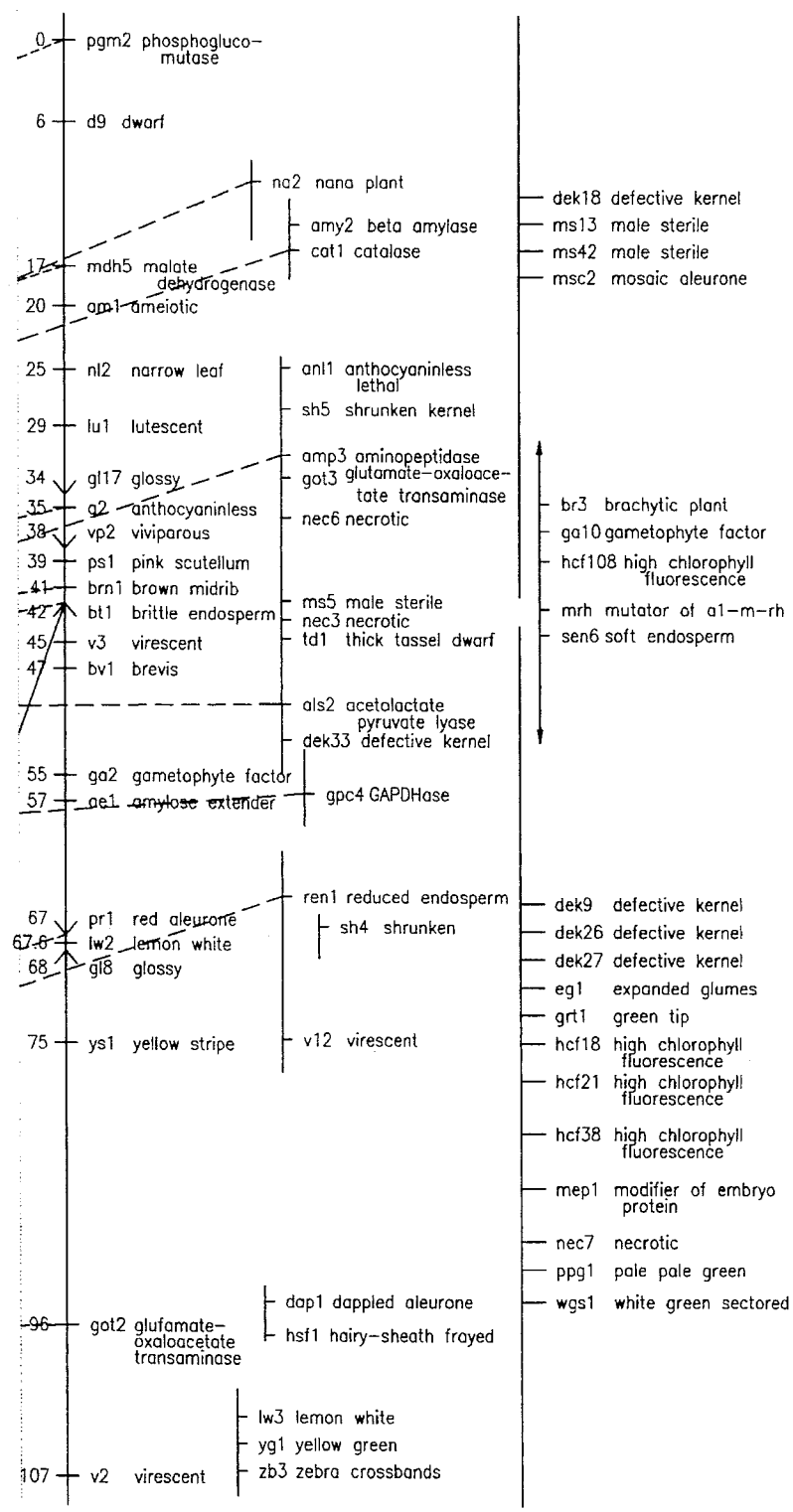
Figure 3K:
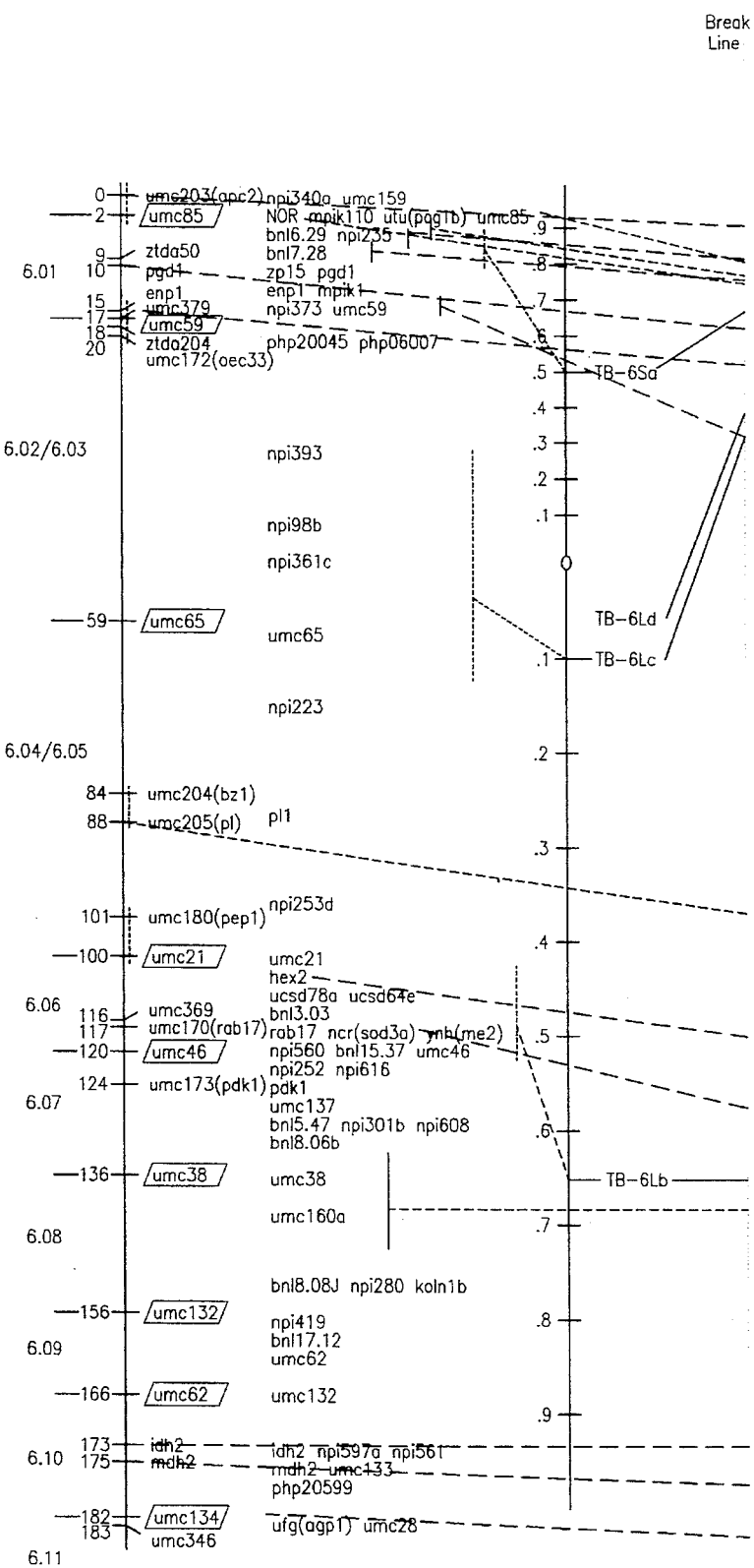
Figure 3L:
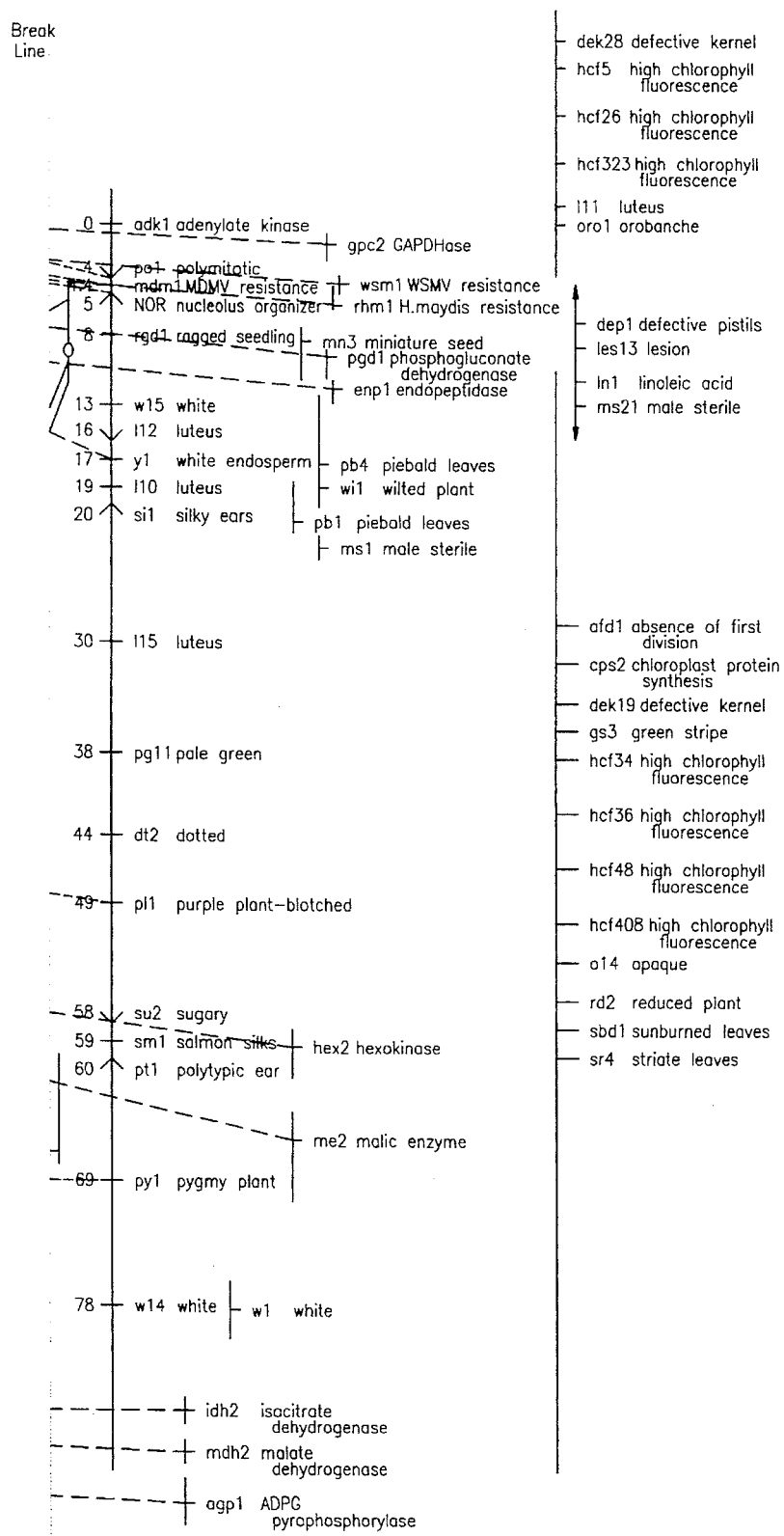
Figure 3M:
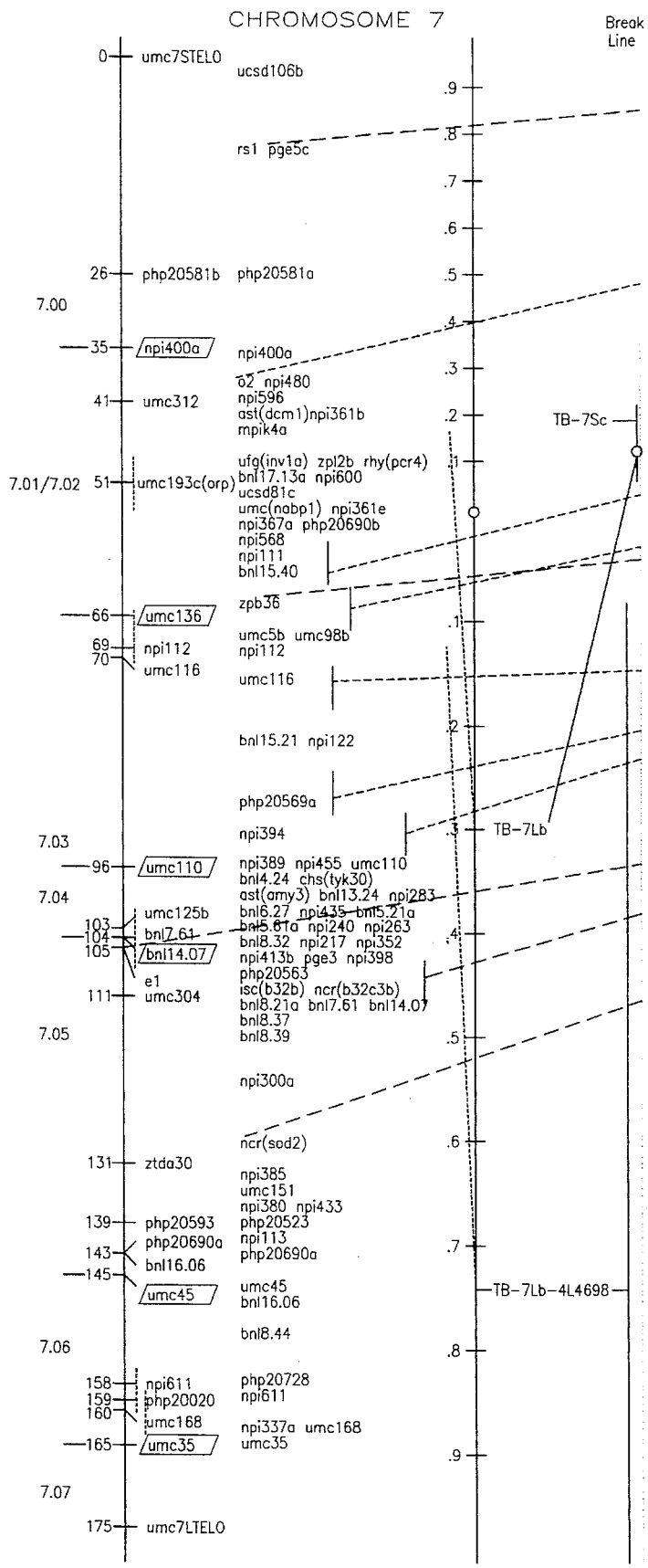
Figure 3N:
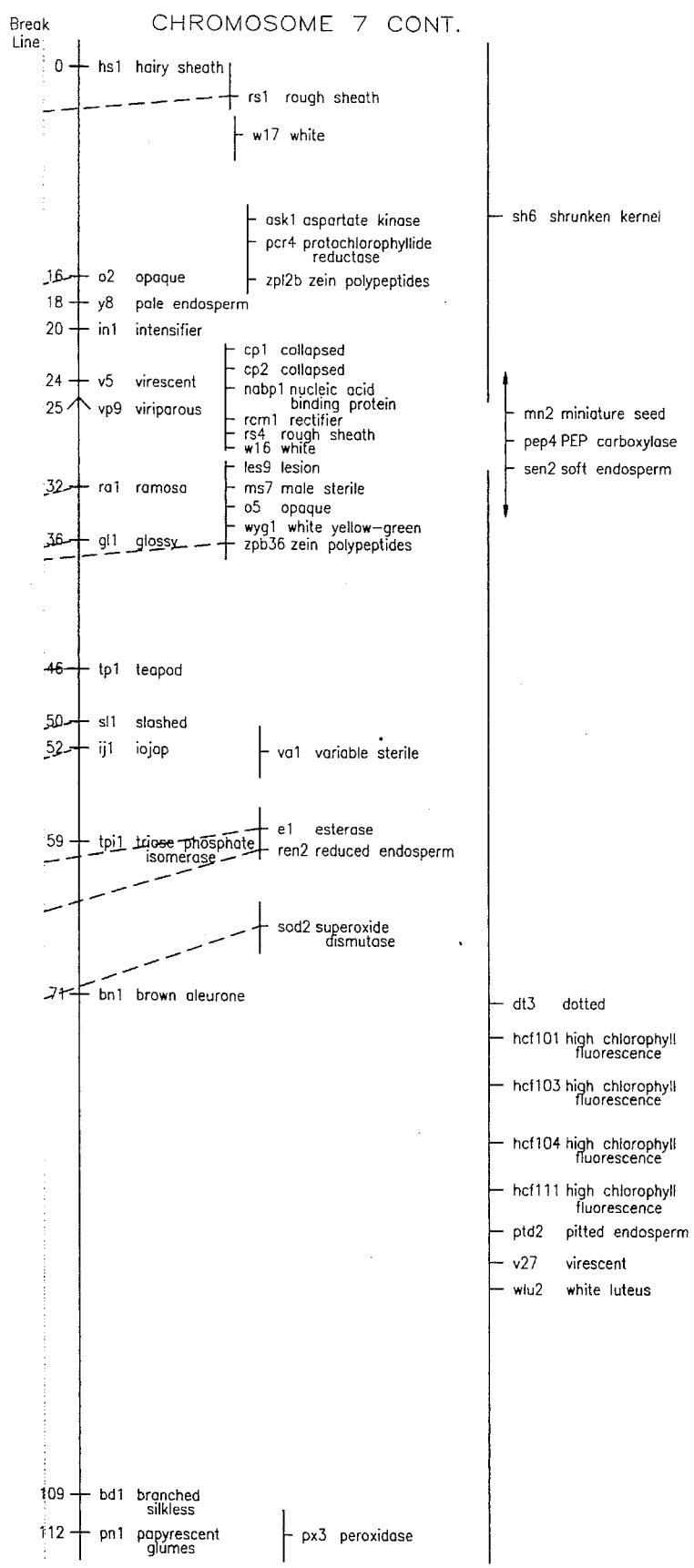
Figure 30:
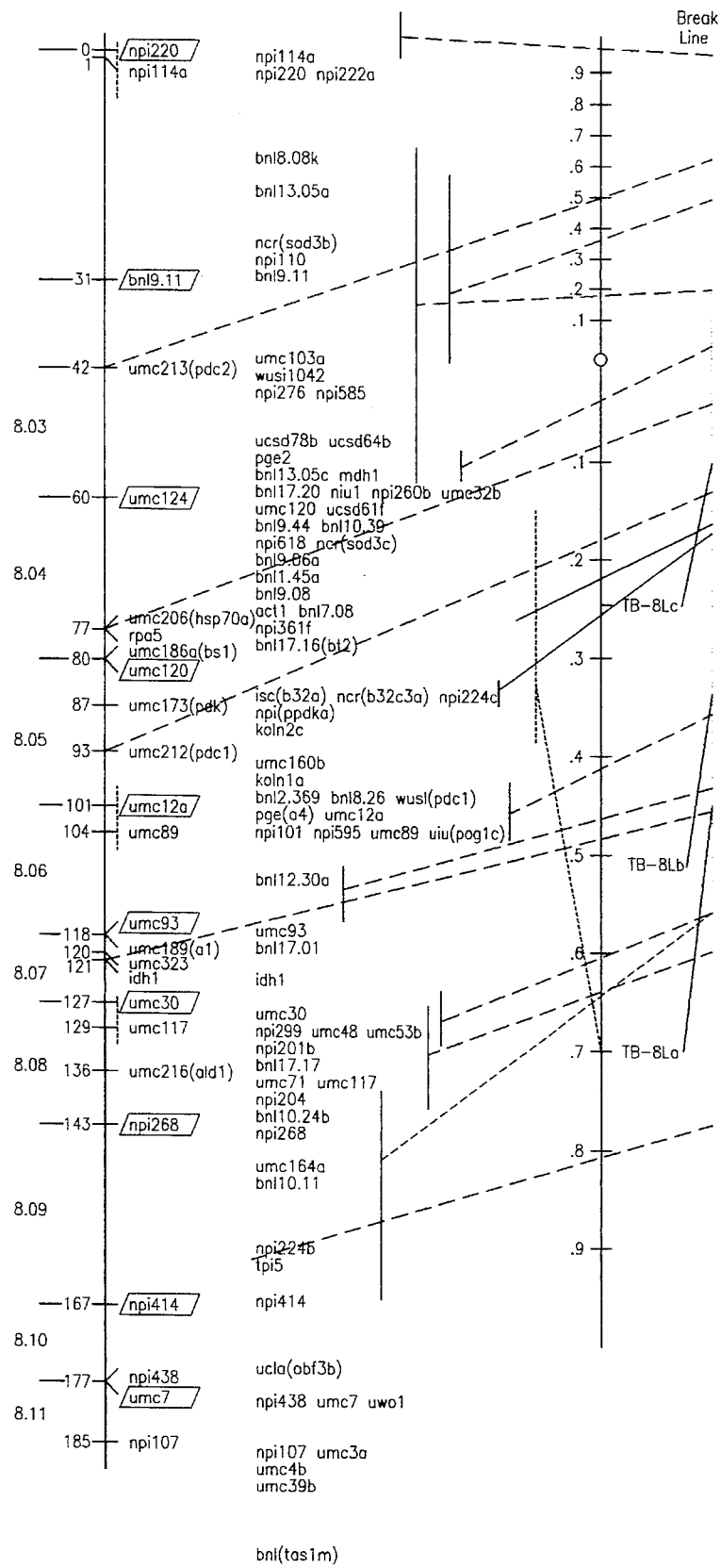
Figure 3P:
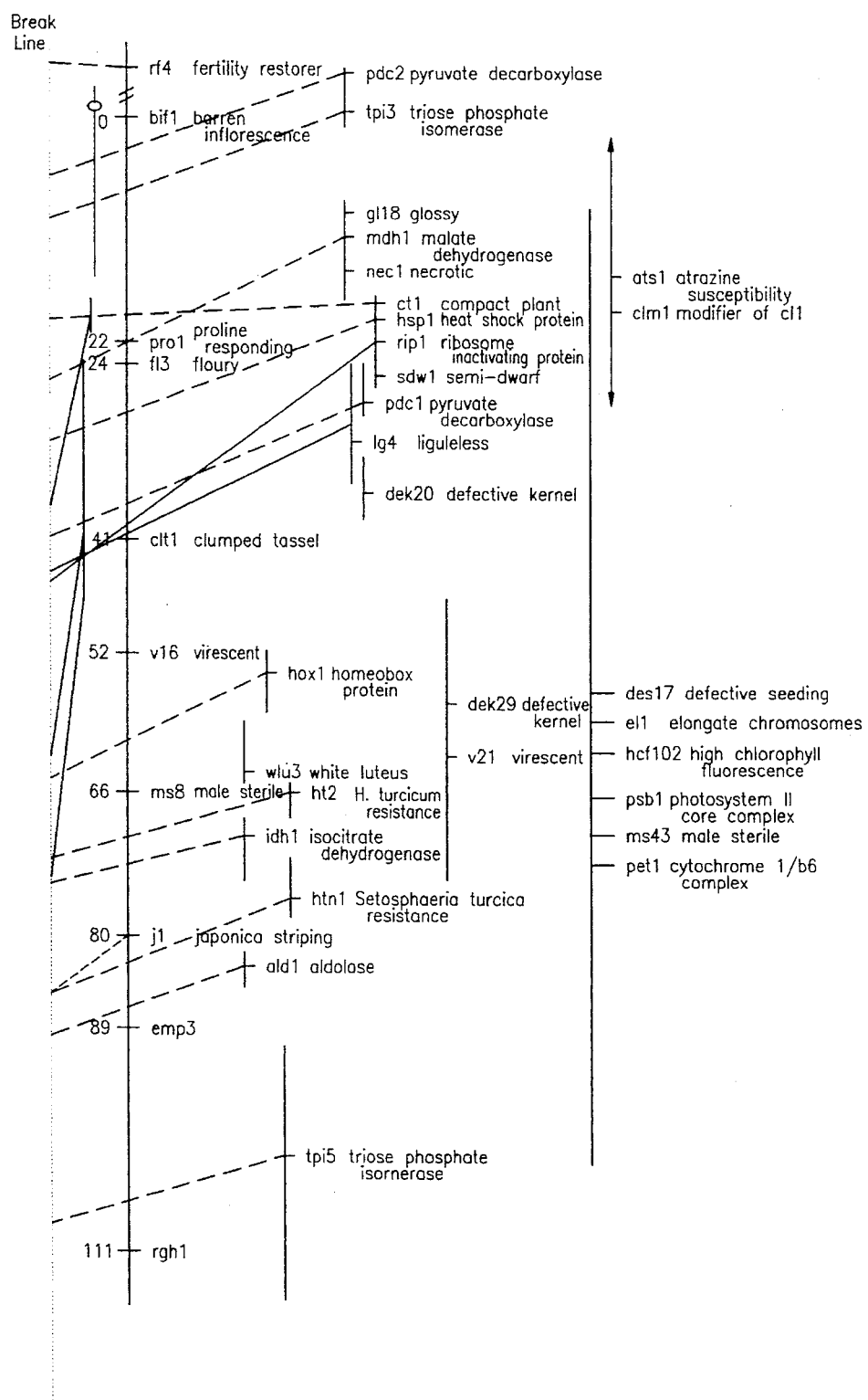
Figure 3Q:
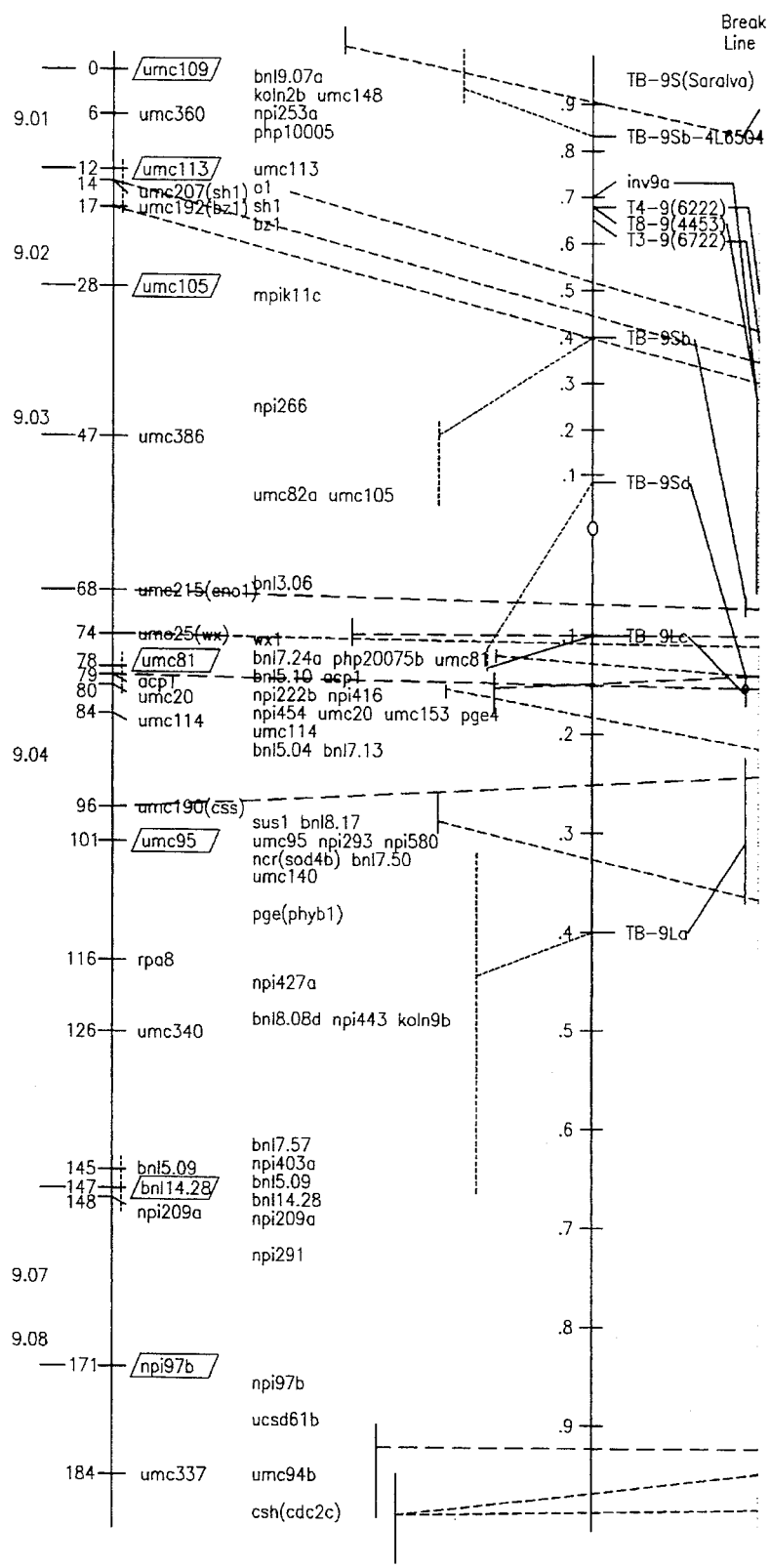
Figure 3R:
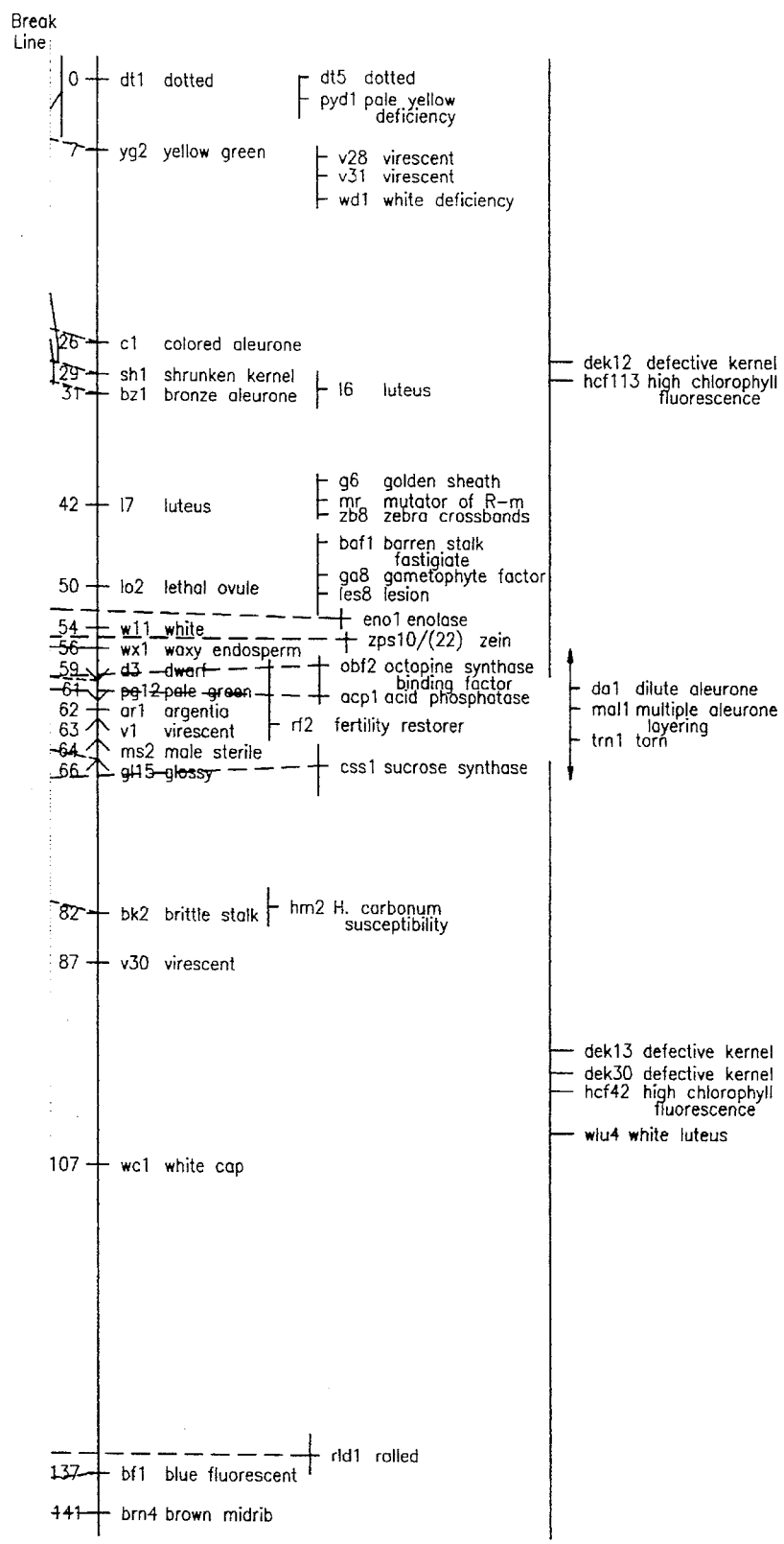
Figure 3S:
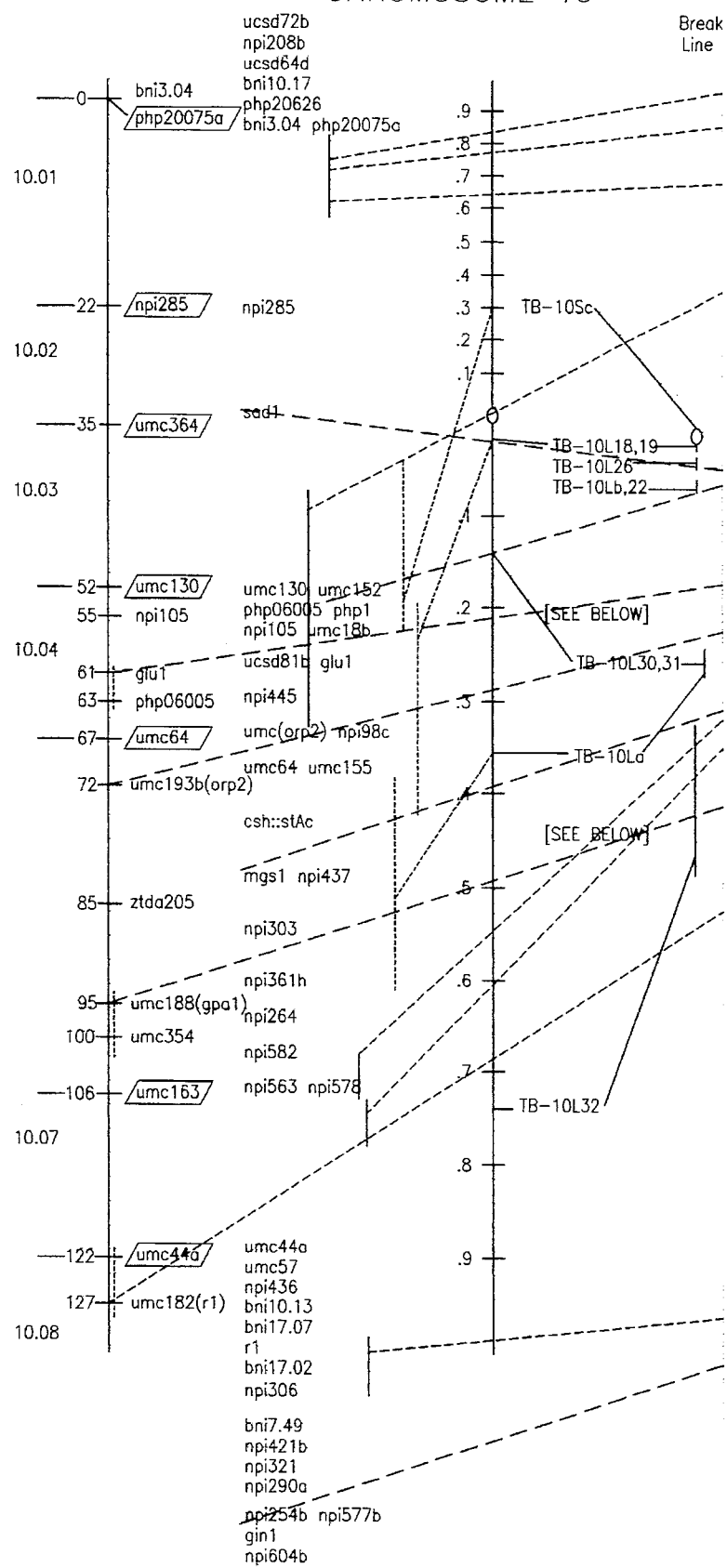
Figure 3T:
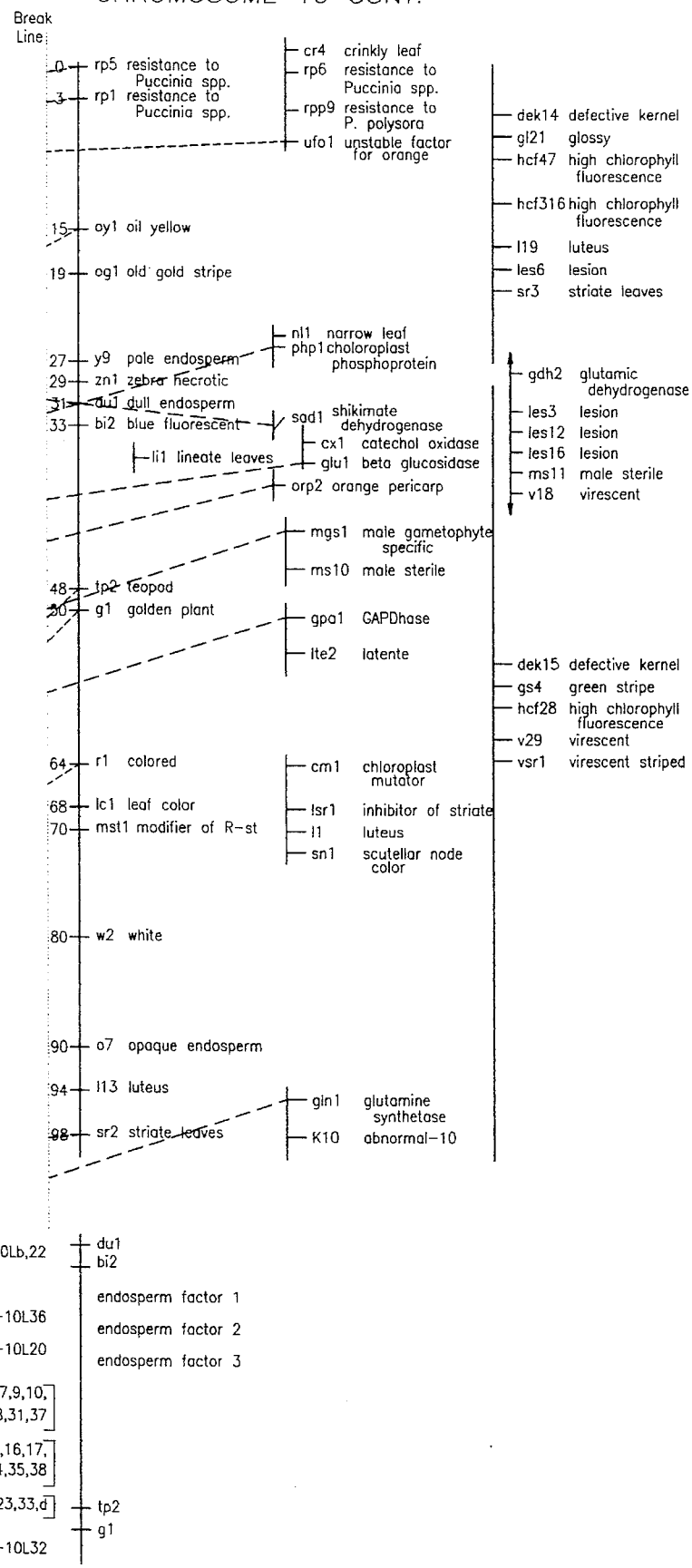

Probes U0050 (UMC50 on FIG. 3) and N0296 (NPI 296 on FIG. 3) on chromosome three are significant at the 0.05 probability level. U0050 has a YY cumulative score mean of 8.57 and ZZ of 6.66. N0296 has a YY mean of 8.54 and a ZZ of 7.45. Although not significant at the 0.05 level, there is an indication that the YY plant contributes some MSR to MCDV in the chromosomal regions around probes U0042 through U0066 on chromosome four. On chromosome five U0054 is statistically significant, having YY average score 8.56 and ZZ 6.60. Closely associated probe U0126 is highly significant, with average YY at 8.76 and ZZ at 6.60. Probes N0264, U0064 and N0445 are also highly significant. N0264 has mean YY of 8.87 and ZZ of 6.16. U0064 has a YY cumulative average 8.93 and ZZ 6.77. N0445 has YY mean of 8.71 and ZZ of 6.87. Probes which were statistically significant but which were not surrounded by other probes with at least the 0.05 level of significance were usually disregarded. The following probes were in this disregarded category: U0044, U0109, U0089, U0028, B1521, U0056, U0052, N0213, U0063, U0026, U0127, N0401.

The results of the RFLP analysis indicated that the following chromosomal regions (identified on the Table below) on Mp705 and Va35 carried the genetic material responsible for MSR to MCDV.

| | | | MAIZE CHLOROTIC DWARF VIRUS TOLERANCE Va35/Mp705 $F_2$ POPULATION | | | | | |
|---|---|---|---|---|---|---|---|---|
| CHR # | PR > F | R-Sq. | FALC. A | EST. EFFECT | GENE** ACTION | DONOR PARENT | FLANKING PROBES | PROBE DIST.* |
| 1 | 0.001 | 0.08 | 1.2 | 2.4 | ADDIT. | Mp705 | U67-U119 | 11 |
| 1 | 0.01 | 0.06 | 1.04 | 2.08 | ADDIT. | Mp705 | N120-U107 | 20 |
| 3 | 0.01 | 0.06 | 0.96 | 1.91 | ADDIT. | Mp705 | N446-N296 | 31 |
| 4 | 0.1 | 0.03 | 0.66 | 1.33 | RECESS | Va35 | U42-N396 | 12 |
| 5 | 0.001 | 0.07 | 1.08 | 2.16 | ADDIT. | Mp705 | U54-N239 | 10 |
| 7 | 0.04 | 0.04 | 0.63 | 1.27 | RECESS | Mp705 | N455-U110 | 3 |
| 10 | 0.001 | 0.14 | 1.35 | 2.71 | RECESS | Mp705 | U64-N563 | 14 |

Chromosomal regions with major MCDV effects.
*Distance in cM between probes capping the chromosomal regions.
**DOMIN. = DOMINANT GENE ACTION
ADDIT. = ADDITIVE GENE ACTION
RECESS. = RECESSIVE GENE ACTION The plant source of the genetic material associated with the listed probes is indicated in FIG. 1. Negative signs indicate the source of resistance is the susceptible parent, no sign (i.e. positive) indicates the source is the resistant parent. The probes are listed by their first letter and their number, i.e. probe on BNL7.25 (as listed on FIG. 3) is listed on FIG. 1 as BO725. The large numbers bolded under the heading "Sum" indicate the statistically significant associations between the trait and the chromosomal region associated with the corresponding RFLP probe. FIG. 2 shows selected probes between which the genetic material evidenced mild symptomatic response in the ZZ plant (genetic information R-sq.=estimated proportion of total variation associated with the RFLP probe based on the difference between rated symptoms of the homozygous resistant and homozygous susceptible allele class.

PR>F=probability of chance occurrence.

FALC A=estimate of half the difference in true homozygous class means, Falconer's 'a'.

The data gathered indicated the susceptible parent Va35 may have some genetic material that expresses MSR to MCDV. This chromosomal material is flanked by U42-N396 probes which is a probe distance of 23 cM map units on chromosome four. Because it was only a slight contribution and the gene action was recessive, further study of this chromosomal region was not pursued and it was not introgressed into the elite material.

Similarly, the data gathered indicated chromosomal material on chromosome one between probes N120 and U107, a distance of 20 cM, was expressing some MSR to MCDV. However, the reliability of the probes employed in that region are suspect and thus further study and introgression of that region into elite inbred material was not pursued.

Linkage block one, locus 1, is the genetic material located between Map Unit 111 and Map Unit 152 proximate flanking probes U67-U 119 on chromosome one on the centromere proximate to the proximal end of the short arm of chromosome one and opposite the proximal end of the long arm of chromosome one.

Linkage block three, locus 2, is the genetic material located between Map Unit 55 and Map Unit 108 proximate probes UMC92, UMC82 or probes N446-N296 and located on chromosome three on the chromosomal region proximate the interconnect of the proximal end of the short arm of chromosome three and the first end of the centromere. The second end of the centromere being opposite the first end and proximate the proximal end of the long arm of chromosome three.

Linkage block 5, locus 3, is the genetic material located between Map Unit 88 and Map Unit 141 proximate flanking probes UMC40 -UMC54 possibly between probes UMC126 Map Unit 139 and UMC54 Map Unit 141. flanking probes U54-N239 on the long arm of chromosome 5 opposite the short arm of chromosome five.

Linkage block 7, locus 4, is the genetic material located between Map Unit 96 and Map Unit 103 proximate probes UMC110 and NPI283 possibly between flanking probes N445 and U110 on the long arm of chromosome seven. The long arm of chromosome seven being opposite to the short arm of chromosome seven.

Linkage block 10, locus 5, is the genetic material located between Map Unit 67 and Map Unit 106 between UMC6 and UMC354 flanking probes U64-N563 and located on the long arm of chromosome 10. The long arm being opposite the short of ten and having a distal proximal end. The proximal end of long arm ten being located proximate the second end of said centromere.

FIG. 3 shows a public map showing the probes that lay within the linkage blocks of genetic material which give rise to the MSR to MCDV. FIG. 4 shows mapping of additional probes in the areas of interest. Table 1 lists these and other probes within and near the map units of interest. If a probe is not available any substitute probes that map in the area of interest can be made and or employed in the scope of the present invention.

Once the linkage blocks were identified, the additional probes which map into the linkage blocks were utilized to closely define the desired genetic region. It is emphasized that this invention may be practiced using any molecular markers which map in the regions of the map at the locations indicated, provided that the markers are polymorphic for the cross.

FIG. 4 shows probes in the sections of the maize chromosomes of interest. The donor parent Mp705 carries significantly detrimental agronomic characteristics. Thus it was necessary to identify the chromosomal regions of interest as closely as possible so that when introgressing the linkage blocks 1, 3, 5, 7 and 10 into elite germplasm, only the desired MSR to MCDV is transferred into the genome of the resultant inbred and likewise hybrid combination. Thus to generate a commercially viable inbred, the beginning crossover event (the crossover closest to the distal end of the short arm of the respective chromosome) and the ending crossover event (the crossover closest to the distal end of the long arm of the respective chromosome) must occur with precision and accuracy to avoid carrying excessive genetic material from Mp705 into the resultant inbred. Of course if the donor material is elite material which by this invention has the precise crossover events therein, then the carry over of some of the elite genetic material into the new progeny is not necessarily detrimental. However to generate the first introgressed plant at loci 1–5 the crossover events were critical. Thus the following additional probes were employed in the chromosomal regions of interest to more closely identify where the MSR to MCDV genetic material is located on the respective chromosome.

Table 1 corresponds with FIG. 2 and shows homozygous class differences in the average score for each rating, i.e. mean of YY class minus mean of ZZ class. The scores in parenthesis include all data except for experiment 6. The scores without parenthesis included all data for all experiments.

TABLE 1

| | SECTION 2 | | | | | | |
|---|---|---|---|---|---|---|---|
| | | | | | Number of Plants in each Class | | |
| | VB | TT | CHL | CUM | YY | YZ | ZZ |
| NPI401 | .44(.48) | .37(.48) | .32(.44) | 1.13(1.41) | 70 | 117 | 40 |
| UMC167 | .72(.87) | .52(.68) | .65(.85) | 1.89(2.40) | 52 | 135 | 54 |
| BNL5.59 | .80(.80) | .67(.66) | .80(.80) | 2.27(2.26) | 23 | 50 | 20 |
| UMC119 | .45(.80) | .36(.62) | .39(.76) | 1.2 (2.18) | 69 | 91 | 43 |
| | SECTION 3 | | | | | | |
| | VB | TT | CHL | CUM | N YY | YZ | ZZ |
| BNL8.15 | .27 | .08 | .06 | .42 | 57 | 152 | 80 |
| NPI446A | .36(.42) | .29(.39) | .33(.43) | .98(1.24) | 77 | 137 | 57 |
| BNL5.59 | .61(.72) | .42(.45) | .63(.74) | 1.66(1.91) | 59 | 118 | 50 |
| NPI296 | .09(.37) | .18(.38) | .17(.35) | .43(1.09) | 66 | 131 | 43 |

TABLE 1-continued

SECTION 4

|  | VB | TT | CHL | CUM | N YY | YZ | ZZ |
|---|---|---|---|---|---|---|---|
| BNL5.71 | .24(.21) | .11(.09) | .24(.32) | .60(.63) | 51 | 128 | 47 |
| UMC54 | .73(.78) | .33(.37) | .70(.81) | 1.76(1.96) | 65 | 121 | 43 |
| UMC126 | .76(.83) | .46(.52) | .73(.81) | 1.95(2.16) | 54 | 126 | 53 |
| NPI239 | .53(.35) | .43(.43) | .41(.22) | 1.36(1.00) | 93 | 134 | 41 |

SECTION 5

|  | VB | TT | CHL | CUM | N YY | YZ | ZZ |
|---|---|---|---|---|---|---|---|
| NPI455 | .42(.37) | .21(.28) | .33(.27) | .95(.93) | 47 | 117 | 50 |
| UMC56 | .33(.50) | .32(.45) | .29(.32) | .94(1.27) | 59 | 98 | 65 |
| UMC110 | .37(.58) | .32(.46) | .34(.38) | 1.04(1.42) | 64 | 97 | 64 |
| BNL14.07 | .05(.09) | .08(.15) | .07 | .10 | 77 | 94 | 48 |
| NPI433 | .26 | .13 | .31 | .71 | 69 | 150 | 63 |
| BNL15.21 | .63 | .47 | .36 | 1.46 | 51 | 73 | 25 |

SECTION 6

|  | VB | TT | CHL | CUM | N YY | YZ | ZZ |
|---|---|---|---|---|---|---|---|
| NPI455 | .67(.75) | .33(.40) | .59(.68) | 1.59(1.84) | 75 | 146 | 74 |
| UMC64 | .81(.77) | .56(.63) | .71(.77) | 2.09(2.16) | 44 | 139 | 44 |
| NPI264 | .82(1.09) | .45(.58) | .78(1.04) | 2.05(2.71) | 73 | 154 | 69 |
| NPI306 |  |  |  |  | 25 | 89 | 30 |
| UMC44A | .42 | .38 | .37 | 1.17 | 32 | 144 | 49 |

The following probes were examined to access the preferred locations of the first crossover event on chromosome one and the second crossover event on chromosome one: NPI234, UMC13, NPI286, UMC29, NPI262, BNL7.21, NPI453, NPI401, NPI598, NPI214, UMC167, NPI279, UMC67, NPI429, NPI272, NPI258, BNL5.59, UMC119, NPI566, NPI605, UMC33, NPL236, NPL447, UMC37. The chromosomal region containing the gene of interest is most likely between UMC67 and NPI272 or BNL5.59. The gene of interest is definitely between UMC67 and UMC 119 on the centromere of chromosome one.

Thus the crossover events are between UMC67 and NPI214 for the first crossover on chromosome one. The second crossover event on chromosome one is between UMC119 and NPI566. As additional locating data is generated, this crossover event will become closer to the actual gene location. However, these two crossover events are relatively close and thus very little undesired genetic material will be introgressed into the resultant hybrid. The crossover events are clearly defined by map units on FIG. 4.

The following probes were examined to access the preferred locations of the first and second events on the short arm of chromosome three: UMC32, BNL8.15, UMC121, NPI446A, UMC154, NPI344A, BNL8.35, UMC46, UMC50, UMC92, UMC10, NPI247, BNL8.23, NBL5.37, NPI296, NPI103, I139. The first crossover event occurs approximate N446 and U50 and contained the U50 site. The second crossover event occurs between UMC102 and NPI296. The second crossover event may ultimately be near BNL8.23 or BNL5.37 or I139. However, until the region is more closely mapped, the second crossover event is proximate NPI296 on the short arm of chromosome three.

The following probes were studied to accurately map the linkage block on the long arm of chromosome five to determine the preferred first and second crossover events which would permit the introgression of the desired chromosomal material that carries the MSR to MCDV to the resultant elite and ultimately to the hybrid made with the elite. The probes include: BNL5.02, BNL7.71, NPI571, NPI449, NPI295, BNL5.71, NPI562, BNL10.12, UMC54, UMC126, UMC141, UMC51, NPI237, NPI239, NPI115, NPI412, NPI458, NPI452, NPI442, NPI313, NPI562, NPI108, UMC68, NPI363, NPI288, BNL5.24, UMC104A. The first crossover event is between B5.71 and U54 (proximate U54) and the second crossover event is preferable between NPI239 and NPI442 proximate NPI239. As more probes are mapped within this area of interest, the crossover events can be more closely tailored to the linkage block desired. The linkage block between UNC54 and NPI239 is sufficient to permit a clean introgression of the desired material without undue carry through of agronomically unacceptable traits.

Turning to the long arm of chromosome seven, the locations of the first and second crossover events, defining the chromosomal linkage block that is introgressed into the elite to produce the desired MSR to MCDV trait, were identified. The following probes were utilized to clearly demark this region: NPI391, BNL15.40, UMC136, NPI122, UMC116, BNL15.21, NPI389, UMC56, NPI263, UMC110, NPI240, BNL7,61, BNL8.21, BNL14.07, NPI385, NPI380, NPI433, NPIN113, BNL16.06, UMC45, UMC35. The chromosomal region of interest appears to be located between NPI455 and U110, thus a crossover should occur proximate NPI455 and a second crossover even should occur proximate UMC110. To assert that the genetic material is present, the first crossover event is located between UMC116 and UMC110 and the second crossover event is located between UM556 and NPI283 (close to NPI283).

The final linkage block carrying the desired MSR to MCDV was located on chromosome ten between flanking probes UMC64 - NPI563. The following probes were employed: UMC130, NPI105, UMC18B, NPI445, UMC64, UMC155, NPI303, NPI437, NPI264, NPI582, NPI563, NPI578, NPI269B, NPI306, UMC44A, UMC57A, UMC66B, BNL10.13, NPI254. The flanking probes were identified as U64 and N563. Thus, the linkage block of chromosomal material that contained the desired trait is located between NPI445 and NPI563. The trait appears to be closely associated with the probes UMC64 and especially with probe NPI264. Thus, the first crossover event is between NPI445 and UMC64 and the second crossover event is between NPI269B, NPI563 closest to NPI563.

It should be readily understood in the art that the other probes which more closely map the linkage block as identified by the map units could be employed to identify the crossover events. The linkage blocks listed on the table above (between flanking probes) are located at the map locations because the trait is transferred without the transfer of undesirable traits from the donor of the trait. Larger linkage blocks could likewise be transferred within the scope of this invention as long as the material introgressed is sufficiently tailored to avoid transfer of undesirable traits into the resultant plant. It will be appreciated that breeding efforts which seek to improve agronomic traits while attaining MCDV resistance are empowered by the arrangement of the superior allele in the linkage blocks.

Chromosome region one is the genetic material expressing the desired trait between flanking probes UMC67 and UMC 119.

Chromosome region two (on chromosome three) is the genetic material expressing the desired trait between flanking probes NPI446 - NPI296.

Chromosome region three (on chromosome five) is the genetic material expressing the desired trait between flanking probes UMC54 - NPI239.

Chromosome region four (on chromosome seven) is the genetic material expressing the desired trait between flanking probes NPI455 - UMC110.

Chromosome region five (on chromosome ten) is the genetic material expressing the desired trait between flanking probes UMC64 - NPI563.

Once the chromosomal regions associated with the MSR to MCDV were identified, the regions could be precisely and accurately introgressed from the MCDV resistant donor into an elite inbred which has desirable agronomic traits. Ultimately, the trait could be introgressed "cleanly" from one elite inbred into another elite inbred. Ultimately, a resultant hybrid which as MSR to MCDV could be produced. It should be understood that a variety of hybrids with this trait could be developed and seed therefore produced and sold to farmers for maize production in MCDV prone areas as well as in other locations.

As stated herein, the objective of this invention is to improve the resistance to MCDV of elite breeding lines without substantially affecting their combining ability. The term "elite" is a term of the art and its meaning is well known. Many factors contribute to the elite nature of these breeding lines but of these factors the yield, in hybrid combination, and the moisture content of the seed, percentages of root and stalk lodging are important. In performing this invention, then, the introgression of the MSR trait can be monitored from generation to generation and, most importantly, the progressive restoration of the genetic background of the elite germplasm may also be observed. The best selections made by using RFLP fingerprinting ultimately require field testing with MCDV infestation in order that the mild symptomatic response trait may be confirmed and that the restoration of the elite character derived from the elite parent germplasm may also be confirmed. However, in this case the numbers of lines requiring such testing is very low compared with the very high numbers which would otherwise be required. Ideally, the product line should have the same combining ability as its elite MCDV-non mild symptomatic response parent combined with the mild symptomatic response character of its resistant parent.

The principal feature of this invention is the transfer of genes from a relatively resistant donor to a relatively susceptible recipient. However, the level of mild symptomatic response of the donor and recipient lines is, of course, relative and the non mild symptomatic response of the recipient may itself possess mild symptomatic response genes which may usefully be retained in the genome of the improved lines.

By virtue of this invention it is now possible to use molecular markers to introgress the MCDV mild symptomatic response trait from Mp705, or from ancestors, sibling, or progeny thereof, into elite but susceptible lines. The following example outlines the introgression of the identified linkage block into an inbred designated ZS211. ZS211 is a yellow dent corn. The introgression of the desired linkage block resulted in an improved inbred designated ZS211:MCDV.

The following example outlines the introgression of the five linkage blocks expressing the desired trait into an inbred designated ZS211 which is an elite inbred that has agronomically desirable traits including low percentage of moisture, root lodging and stalk lodging, and high yield results. It should be understood that introgression of less than all five linkage blocks is within the scope of this invention as long as the resultant plant evidences virus tolerance. Likewise, the use of conventional breeding techniques to transfer the trait from elite inbreds into other germplasm is contemplated.

In the corn breeding nursery the following plants were grown:

ZS211 was crossed as a female to Mp705 forming a population ZS211Mp705. The seed from the cross between ZS211 and Mp705 was encoded. This was an $F_1$ generation. The seed was planted in a winter nursery in Hawaii where it was selfed to produce to $F_2$ generation encoded. The seed from the $F_2$ generation was screened using the greenhouse bioassay in Wooster, Ohio, to determine whether or not MCDV resistance was present in the select seed.

Specific plants were identified as a result of the screen as having mild symptom expression. These MSR plants were selfed; however, it was clear that the primary candidate of these would not be able to produce seed due to its weakened condition. Plant 536 was selected as it appeared to have the best genetic makeup combined with a mild symptom expression. However, plant 536 could not produce seed; thus, the pollen from plant 536 was crossed onto an inbred which is a publicly available line designated B68HT. Thus a new $F_1$ generation was created. B68HT is in the same relative heterotic group as ZS211 and so there was little to no disruption of the potential combining ability and agronomic traits of future selections from this $F_1$. The newly created $F_1$ was encoded. It was grown and the plants were sampled for DNA. Those with the appropriate MCDV regions were backcrossed onto ZS211. This created a backcross 1 which was designated as ZS211MCDVBackcross 1. The population created from plant number 11 was crossed onto ZS211 and planted in the nursery in Hawaii. Samples were taken. Plants were selected based on the RFLP's. The selected plants were again backcrossed to ZS211. These were encoded ZS211MCDVBackcross 2. The selected plant from that population was plant number 197 and it was crossed onto ZS211 and was then planted in the summer of 1992. Samples were taken and plants were selected based on RFLP's and backcrossed again onto ZS211. The population created from plant number 356 was crossed onto ZS211 in 1992 summer nursery and seeds were planted in the winter nursery in Hawaii. All plants were sampled and selfed. The selfed seed of plant number 143 and 168 based on the RFLP selections were planted in the nursery in Slater. These plants were sampled and selfed. The selfed seed from plant 48 from the BC3S1 family 143 and plant 1 from the BC3S1 family 168 were planted in Hawaii. Samples were taken and the plants were again selfed. The process was completed until a inbred homozygous at all 5 loci was developed.

Because the gene action on chromosomes one, three and five at the loci one, two, and three respectively (loci being the material within the flanking probes on each respective chromosome) is additive gene action and the gene action on chromosomes seven, ten at loci four and five respectively is recessive gene action, the transfer of the MCDV trait to the hybrid is best effected by crossing two inbred lines, male and female, each having the full complement of homozygous genetic material at all locations.

Fixing the five regions in either the male or female inbred alone reduces the expression of the trait by at least ⅖th (the recessive action genes on seven and ten are usually not expressed) but the additive action genes are expressed, through the degree of expression varies. Alternatively, the additive genes on chromosome one, three and five can be fixed in one inbred and the recessive genes disregarded. Alternatively one inbred can have all five loci and the second only have the fourth and fifth loci with resistant alleles. The additive genes can likewise be fixed in both inbreds or some additive genes can be in one inbred and other additive genes can be in the second inbred so the hybrid receives the full complement. It would achieve the greatest MCDV resistance in the resultant plant if both male and female inbreds were fixed for all five gene locations. This, however, greatly limits the flexibility of a corn breeding program as each parent of the hybrid requires introgression of the chromosome material. To this end, ZS211 has been repeatedly backcrossed with Mp705 and plant material has been selected by review of RFLP data for first and second crossover events proximate the flanking probes of the respective loci and the remaining genetic material reflects the ZS211 genotype. ZS211 is most often used as the female. The ZS211 inbred which is resistant to MCDV developed by this process is designated ZS211:MCDV. The full complement of loci one–five are present in ZS211:MCDV so that it can be crossed with a susceptible MCDV inbred or a tolerant MCDV inbred or a resistant MCDV inbred.

Depending on the other parent employed in the cross, the resultant hybrid expresses a high tolerance or resistance to MCDV. Some areas of the corn growing region are more prone to MCDV infection than are other regions, thus in some areas the hybrids expressing resistance in all five loci will be the most attractive to the farmer. In most other areas less prone to virus devastation a high tolerance (but not at all 5 loci) to MCDV is sufficient to combat the disease problem. To develop the most resistant hybrid a male inbred must also be developed, to that end the male ZS053 was twice backcrossed to Mp705 to fix the gene at the loci one-five forming ZS053BC2. When segregation of the desired traits no longer occurs the resultant ZS053 is then selfed repeatedly to establish the desirable agronomic genotype of ZS053 in the resultant ZS053:MCDV. ZS053 is usually used as a male. The resultant hybrid from ZS211 MCDV and ZS053:MCDV shall contain the full complement of the chromosomal material that expresses resistance to MCDV.

This invention provides a repeatable method of obtaining MCDV resistant inbred lines having the elite characteristics and the MCDV resistance which can be employed to produce commercially acceptable hybrids.

Although the foregoing invention has been described in some detail by way of illustration and example for purposes of clarity and understanding, it will be obvious that certain changes and modifications may be practiced within the scope of the invention.

We claim:

1. An elite inbred maize plant and parts thereof being derived from and comprising a genome, homozygous with respect to genetic alleles situated on chromosomes 1, 3 and 5 which are non-native to a first parent of said elite inbred and native to a second parent of said elite inbred, said second parent line selected from the group consisting of maize inbred Mp705, seed of plant introduction No. PI550546, resistant progeny and resistant hybrids thereof, wherein said elite inbred maize line exhibits resistance to MCDV in hybrid combination not significantly less than that of the second parent in the same hybrid combination and yield and moisture characteristics which are not significantly different than the first parent in the same hybrid combination.

2. A maize plant having resistance to MCDV, in a non-Mp705 genomic background, the genome of which contains alleles from the group consisting of Mp705, resistant progeny and resistant hybrids thereof associated with MCDV resistance from at least two loci selected from the group consisting of: (locus 1) chromosome 1, between map units 111 and 152; (locus 2) chromosome 3, between map units 55 and 108; (locus 3) chromosome 5, between map units 88 and 141; locus (4) chromosome 7, between map units 96 and 103; (locus 5) chromosome 10, between map units 67 and 106, references to map units and chromosomal locations as set forth in the maize chromosome map published for the 1993 Maize Genetics Cooperation NewsLetter, Mar. 15, 1993 at FIG. 3.

3. A plant according to claim 2 which is homozygous at each of the selected loci.

4. A method for the production of an inbred maize plant adapted for conferring, in hybrid combination with a suitable second inbred, resistance to MCDV, comprising:

a) selecting a first donor parental line possessing the desired MCDV resistance;

b) crossing the donor line with a second inbred parental line, high yielding in hybrid combination, to produce a segregating population;

c) screening the population for a member having loci associated with the resistance trait selected from the group consisting of: (locus 1) chromosome 1, between map units 111 and 152; (locus 2) chromosome 3, between map units 55 and 108; (locus 3) chromosome 5, between map units 88 and 141; (locus 4) chromosome 7, between map units 96 and 103; (locus 5) chromosome 10, between map units 67 and 106, references to map units and chromosomal locations as set forth in the maize chromosome map published for the 1993 Maize Genetics Cooperation NewsLetter, Mar. 15, 1993 at FIG. 3;

d) selecting the member for further crossing and selection; and c) repeating the procedure until an inbred line is obtained which is homozygous for the resistance trait at the selected chromosome region.

* * * * *